(12) United States Patent
Matsuzawa et al.

(10) Patent No.: US 9,028,848 B2
(45) Date of Patent: May 12, 2015

(54) COMPOSITION FOR COSMETICS, COSMETIC, METHOD FOR PRODUCING OIL-IN-WATER EMULSION COSMETIC, AND TWO SEPARATE LAYER-TYPE COSMETIC

(75) Inventors: Makoto Matsuzawa, Yokohama (JP); Azusa Yamaguchi, Yokohama (JP); Aki Goto, Yokohama (JP); Keiichi Oyama, Yokohama (JP)

(73) Assignee: The Nisshin Oillio Group, Ltd., Tokyo (JP)

( * ) Notice: Subject to any disclaimer, the term of this patent is extended or adjusted under 35 U.S.C. 154(b) by 35 days.

(21) Appl. No.: 13/393,293

(22) PCT Filed: Oct. 28, 2010

(86) PCT No.: PCT/JP2010/069152
§ 371 (c)(1),
(2), (4) Date: Feb. 29, 2012

(87) PCT Pub. No.: WO2011/052674
PCT Pub. Date: May 5, 2011

(65) Prior Publication Data
US 2012/0156271 A1    Jun. 21, 2012

(30) Foreign Application Priority Data
Oct. 30, 2009  (JP) .................................. 2009-251371

(51) Int. Cl.
| | | |
|---|---|---|
| A61K 8/03 | (2006.01) |
| A61K 47/44 | (2006.01) |
| A23D 9/00 | (2006.01) |
| A61K 8/37 | (2006.01) |
| A61K 8/86 | (2006.01) |
| A61Q 19/00 | (2006.01) |
| A61K 8/55 | (2006.01) |
| A61Q 1/00 | (2006.01) |
| A61K 8/34 | (2006.01) |
| A61K 8/39 | (2006.01) |
| A61K 8/92 | (2006.01) |

(52) U.S. Cl.
CPC ... *A61K 8/37* (2013.01); *A61K 8/03* (2013.01); *A61K 8/86* (2013.01); *A61Q 19/00* (2013.01); *A61K 8/553* (2013.01); *A61Q 1/00* (2013.01); *A61K 8/345* (2013.01); *A61K 8/39* (2013.01); *A61K 8/922* (2013.01)

(58) Field of Classification Search
CPC ............. A61K 8/03; A61K 8/86; A61K 8/37; A61K 8/922; A61K 8/345; A61K 8/39; A61K 8/553; A61Q 19/00; A61Q 1/00
USPC ............................. 424/401; 514/786; 554/227
See application file for complete search history.

(56) References Cited

U.S. PATENT DOCUMENTS

| | | | | |
|---|---|---|---|---|
| 6,099,829 | A * | 8/2000 | Tiefensee et al. .......... 424/70.16 |
| 2003/0143313 | A1* | 7/2003 | Ikuina et al. .................. 426/607 |
| 2005/0011895 | A1* | 1/2005 | Lin ............................... 220/300 |
| 2005/0124705 | A1* | 6/2005 | Schreiber et al. ............... 516/53 |
| 2006/0093635 | A1* | 5/2006 | Gotou et al. .................. 424/401 |
| 2006/0263399 | A1* | 11/2006 | Yasuno et al. ................ 424/401 |
| 2009/0018358 | A1* | 1/2009 | Kondo et al. ................. 554/227 |

FOREIGN PATENT DOCUMENTS

| | | |
|---|---|---|
| CN | 1285732 A | 2/2001 |
| CN | 1784211 A | 6/2006 |
| JP | 08165218 A | 6/1996 |
| JP | 2001342126 A | 12/2001 |
| JP | 2002053420 A | 2/2002 |
| JP | 2002155029 A | 5/2002 |
| JP | 2003040708 A | 2/2003 |
| JP | 2003261416 A | 9/2003 |
| JP | 2003305355 A | 10/2003 |
| JP | 2005015467 A | 1/2005 |
| JP | 2005089415 A | 4/2005 |
| JP | 2005162691 A | 6/2005 |
| JP | 2006022004 A | 1/2006 |
| JP | 2006050986 A | 2/2006 |
| JP | 2006306841 A | 11/2006 |
| JP | 2008247866 A | 10/2008 |
| JP | 2009126843 A | 6/2009 |
| JP | 2009215283 A | 9/2009 |
| JP | 2010090079 A | 4/2010 |
| WO | 2007074675 A1 | 7/2007 |

OTHER PUBLICATIONS

International Search Report issued in International Patent Application No. PCT/JP2010/069152, dated Jan. 18, 2011, 4 pages.
Chinese Patent Office, Search Report issued in Chinese Patent Application No. 201080038237.9, dated Nov. 7, 2012, 4 pp.
Japanese Patent Office, Office Action issued in corresponding Japanese Patent Application No. 2011-538474 and partial English-language translation, mailed Nov. 18, 2014 (5 pages).
Efficacy, Potency, and Effect of New Cosmetic Material, Ltd. CMC, pp. 627-629 (Aug. 31, 1998). (Explanation of Relevance Included at End of Partial Translation of Office Action).

* cited by examiner

*Primary Examiner* — Blessing M Fubara
(74) *Attorney, Agent, or Firm* — Wood, Herron & Evans, LLP

(57) ABSTRACT

The present invention relates to a composition for cosmetics including a polyglycerol fatty acid ester, which is an ester of polyglycerol having an average degree of polymerization of 4 to 100 with a fatty acid having 2 to 18 carbon atoms, has a hydroxyl value equal to or less than 15 mgKOH/g, and has a specific gravity at 20° C. of 0.96 to 1.15; a cosmetic which includes the composition for cosmetics; a method for producing an oil-in-water emulsion cosmetic which includes mixing the composition for cosmetics; and a two-separate-layer-type cosmetic, which comprises the composition for cosmetics. The present invention relates to the composition for cosmetics which can be appropriately used in producing a cosmetic giving a highly excellent feel in using and having a very good texture, a cosmetic showing a very high stability over time as an emulsion, and a two-separate-layer-type cosmetic.

13 Claims, No Drawings

COMPOSITION FOR COSMETICS, COSMETIC, METHOD FOR PRODUCING OIL-IN-WATER EMULSION COSMETIC, AND TWO SEPARATE LAYER-TYPE COSMETIC

TECHNICAL FIELD

The present invention relates to a composition for cosmetics containing a specific polyglycerol fatty acid ester, a cosmetic containing the composition for the cosmetics, a method of producing an oil-in-water emulsion cosmetic using the composition for the cosmetics, and a two-separate-layer-type cosmetic containing the composition for the cosmetics.

Priority is claimed on Japanese Patent Application No. 2009-251371, filed Oct. 30, 2009, the content of which is incorporated herein by reference.

BACKGROUND ART

Cosmetics are blended with an oil-based agent for various purposes of providing skin occlusiveness or emolliency, and improving a textural feeling. An oil-based agent to be incorporated is required to have a favorable usage feeling, safety, compatibility with other raw materials, and the like. Among these, a polyglycerol fatty acid ester, which is an oil-based agent, exhibits high safety and is therefore generally used as a surfactant and an emulsifier.

Polyglycerol is a general term referring to glycerol polymers, and a representative structure thereof is a linear polymer resulting from dehydration condensation of primary hydroxyl groups of glycerol. Further, polyglycerol embraces, in addition to the linear polymer represented by the following formula (1), a branched polymer resulting from dehydration condensation between primary hydroxyl groups and secondary hydroxyl groups of glycerol, and a cyclic polymer resulting from dehydration condensation between intramolecular hydroxyl groups. Among these three polymer species, a linear polymer is a predominant component, but the content ratio therebetween may vary depending on the production method, the degree of polymerization, or other factors.

[Chem. 1]

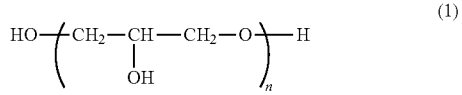

(1)

n: degree of polymerization

Industrially, polyglycerol, which is obtained by a dehydration condensation reaction of glycerol or by recovery of polyglycerol from glycerol distillation residues, has been used in foods or the like, whereas high-purity polyglycerol products, derived from epichlorohydrin, glycidol or the like, have been limited to applications for assay reagents or the like. Further, in the case of polyglycerol from recovery thereof from glycerol distillation residues, such recovery is mainly intended for the production of diglycerol and correspondingly the majority of polyglycerol has been produced through a dehydration condensation reaction of glycerol.

The dehydration condensation reaction of glycerol is a sequential intermolecular dehydration condensation reaction, and polyglycerol obtained by such a reaction exhibits various polymerization degrees and isomeric ratios depending on the reaction conditions. Therefore, the polymerization degree of polyglycerol is generally given in terms of an average degree of polymerization calculated from a measured value of a hydroxyl value.

Polyglycerol for practical use is provided in the form of such a complex mixture. For example, polyglycerol generally referred to as hexaglycerol encompasses monomers and polymers ranging from monomeric glycerol to nonaglycerol having a degree of polymerization of 9, and in terms of polymers thereof, covers isomers as described above.

Since it is generally known that a polyglycerol fatty acid ester exhibits high stickiness, and when blended as an oil-based agent in a large amount in a cosmetic, contributes to deterioration of performance in a usage sensation and texture of cosmetics, a variety of improvements have been attempted therefor (for example, see Patent Document 1).

Further, an oily phase and an aqueous phase are blended into emulsion cosmetics, but aggregation or creaming may take place due to a difference in a specific gravity therebetween. For this reason, it is necessary for a cosmetic to have an appropriate viscosity in order to secure an emulsion stability.

Conventional lotions and emulsions have been used separately from one another for achieving a stability of a preparation. However, recently, from the viewpoint of convenience of use or the like, there is a need for a novel cosmetic which is capable of achieving a usage sensation of both a lotion and an emulsion by means of a single cosmetic. Such a novel cosmetic is required to have fresh texture at a low viscosity due to exhibiting a relatively high moisture content. However, as described above, there is a need in related art for an appropriate viscosity to obtain a cosmetic with a high emulsion stability, and a cosmetic having a high emulsion stability even at a low viscosity (for example, see Patent Documents 2 and 3).

A self-emulsification-type oily liquid cosmetic, when brought into contact with water, undergoes a phase inversion to form an oil-in-water emulsion. Representative examples of the self-emulsification type oily liquid cosmetic include a cleansing cosmetic and a bath cosmetic. The bath cosmetic has been frequently used in bathing for the purpose of preventing rough skin, chapped skin and cracked skin or improving the skin condition. Examples of the bath cosmetic formulation include a bath salt, a bath oil, and a crude drug extract. Among these, a self-emulsification-type oily bath oil type product consisting of a mixed system of an oily component and a surfactant, when put into a bath, undergoes self-emulsification in the bath to result in uniform distribution of a particulate oily component in the bath, whereby a variety of beneficial effects intrinsic to the oily component may be expected such as emolliency, a moisture-retaining property, an anti-inflammatory property, and a warm bath effect. However, products of a self-emulsification-type oily bath oil-type containing a polyglycerol fatty acid ester have a problem associated with a deteriorated usage sensation due to creaming or separation of an oily component after being put into hot water. An attempt has been made to cope with this problem (for example, see Patent Document 4).

Further, as the formulation of a bath agent, there is an emulsion bath agent which is characterized in that an oil-soluble substance and a water-soluble substance may be blended and added without limitation. However, an emulsion bath agent is required to have a low viscosity in terms of a usage characteristic, and therefore has a problem associated with a poor stability over time of the bath additive itself. Therefore, an attempt has been made to address this problem (for example, Patent Documents 5 and 6).

Further, with regard to a two-separate-layer-type cosmetic, there is a need for development of a two-separate-layer-type cosmetic which includes an oily layer and an aqueous layer and exhibits an excellent aesthetic appearance in terms of external appearance, and which can be easily dispersed uniformly by gently shaking before using and, after using, easily separated into the original two layers of an oily layer and an aqueous layer, and remain stable. To this end, a variety of suggestions have been made (for example, see Patent Document 7).

PRIOR ART DOCUMENTS

Patent Documents

[Patent Document 1] Japanese Unexamined Patent Application Publication No. H08-165218
[Patent Document 2] Japanese Unexamined Patent Application Publication No. 2008-247866
[Patent Document 3] Japanese Unexamined Patent Application Publication No. 2009-215283
[Patent Document 4] Japanese Unexamined Patent Application Publication No. 2003-261416
[Patent Document 5] Japanese Unexamined Patent Application Publication No. 2009-126843
[Patent Document 6] Japanese Unexamined Patent Application Publication No. 2001-342126
[Patent Document 7] Japanese Unexamined Patent Application Publication No. 2006-306841

DISCLOSURE OF INVENTION

Problems to be Solved by the Invention

As described above, depending on cosmetics to be used, a variety of properties are required for a composition for cosmetics. However, the composition for cosmetics disclosed in Patent Literature 1 is still insufficient in terms of a usage sensation and texture; the composition for cosmetics disclosed in Patent Literature 2 to 6 is still insufficient in terms of an emulsion stability and a stability over time; and the composition for cosmetics disclosed in Patent Literature 7 is still insufficient in terms of external appearance aesthetics and convenience during use.

Further, with regard to a great variety of cosmetics as described above, there is no composition for cosmetics that can be commonly and favorably used therein, and therefore there is a need for development of such a composition for cosmetics.

Therefore, the present invention has been made in view of the aforesaid situation, and it is an object of the present invention to provide a cosmetic having a superior usage sensation and a very good texture, a cosmetic showing a very high stability over time as an emulsion even though having a low viscosity, and a two-separate-layer-type cosmetic which can be easily dispersed uniformly by lightly shaking before using and, after using, easily separated into the original two layers of an oily layer and an aqueous layer, and remain stable.

Means to Solve the Problems

As a result of a variety of extensive and intensive studies to address the problems as described above, the inventors of the present invention have discovered that by incorporation of a composition for cosmetics containing a polyglycerol fatty acid ester, which is an ester of polyglycerol having an average degree of polymerization of 4 to 100 with a fatty acid having 2 to 18 carbon atoms, has a hydroxyl value equal to or less than 15 mgKOH/g, and has a specific gravity at 20° C. of 0.96 to 1.15, the resulting cosmetic has an excellent feel in using and has a very good texture. Further, the inventors have discovered that the cosmetic has an excellent stability over time as an emulsion even though having a low viscosity, and the resulting two-separate-layer-type cosmetic can be easily dispersed uniformly by lightly shaking before using and, after using, easily separated into the original two layers, including an oily layer and an aqueous layer, and remain stable. The present invention has been completed based on these findings.

That is, the present invention relates to the following.

(1) A composition for cosmetics including a polyglycerol fatty acid ester, which is an ester of polyglycerol having an average degree of polymerization of 4 to 100 with a fatty acid having 2 to 18 carbon atoms, has a hydroxyl value equal to or less than 15 mgKOH/g, and has a specific gravity at 20° C. of 0.96 to 1.15.

(2) The composition for cosmetics according to (1), wherein the polyglycerol constituting the polyglycerol fatty acid ester has an average degree of polymerization of 4 to 10, and the fatty acid constituting the polyglycerol fatty acid ester has a carbon number of 6 to 18.

(3) The composition for cosmetics according to (2), wherein the polyglycerol constituting the polyglycerol fatty acid ester has an average degree of polymerization of 6, and the fatty acid constituting the polyglycerol fatty acid ester has a carbon number of 6 to 10.

(4) The composition for cosmetics according to any one of (1) to (3), wherein the polyglycerol fatty acid ester has a hydroxyl value of 10 mgKOH/g or less.

(5) The composition for cosmetics according to any one of (1) to (4), further including a polyhydric alcohol and a non-ionic surfactant.

(6) The composition for cosmetics according to (5), wherein the polyhydric alcohol is at least one selected from the group consisting of dipropylene glycol, octanediol, 1,3-propanediol and hexanediol.

(7) The composition for cosmetics according to (5) or (6), wherein the non-ionic surfactant is a polyoxyethylene hydrogenated castor oil.

(8) The composition for cosmetics according to any one of (5) to (7), further including a hydrogenated lecithin.

(9) The composition for cosmetics according to any one of (1) to (8), wherein the composition for cosmetics is for a skin care cosmetic, a bath cosmetic, a hair cosmetic, or a make-up cosmetic.

(10) A cosmetic including the composition for cosmetics according to any one of (1) to (9).

(11) The cosmetic according to (10), wherein the cosmetic is a two-separate-layer-type cosmetic, or an emulsion cosmetic.

(12) A method of producing an oil-in-water emulsion cosmetic, including mixing the composition for cosmetics according to any one of (1) to (9) with a hydrophilic solution and emulsifying the mixture.

(13) A two-separate-layer-type cosmetic including the composition for cosmetics according to any one of (1) to (9) and water, packaged in a transparent or translucent container.

Effect of the Invention

Use of the composition for cosmetics of the present invention enables the production of a cosmetic giving an excellent usage sensation and having a very good texture, and a cosmetic showing a very high stability over time as an emulsion even though having a low viscosity. Further, use of the composition for cosmetics of the present invention enables the production of a two-separate-layer-type cosmetic which can be easily dispersed uniformly by lightly shaking before using and, after using, easily separated into the original two layers of an oily layer and an aqueous layer, and remain stable.

EMBODIMENTS OF THE INVENTION

Hereinafter, embodiments of the present invention will be described in more detail.

<<Composition for Cosmetics>>

The composition for cosmetics of the present invention contains a polyglycerol fatty acid ester, which is an ester of polyglycerol having an average degree of polymerization of 4 to 100 with a fatty acid having 2 to 18 carbon atoms, has a hydroxyl value equal to or less than 15 mgKOH/g, and has a specific gravity at 20° C. of 0.96 to 1.15.

In the present invention, the polyglycerol constituting the polyglycerol fatty acid ester has an average degree of polymerization of 4 to 100, preferably 4 to 50, more preferably 4 to 10, and most preferably 6. That is, the polyglycerol of the present invention is more preferably tetraglycerol, pentaglycerol, hexaglycerol, heptaglycerol, octaglycerol, nonaglycerol or decaglycerol, and most preferably hexaglycerol.

If the polyglycerol constituting the polyglycerol fatty acid ester has an average degree of polymerization outside the range of 4 to 100, this undesirably leads to problems associated with a lowering of a specific gravity at 20° C. and poor solubility with other oil-based agents.

In the present invention, the fatty acid constituting the polyglycerol fatty acid ester has a carbon number of 2 to 18, and the fatty acid may be a saturated or unsaturated, linear or branched fatty acid. Examples of the fatty acid having 2 to 18 carbon atoms include a linear saturated fatty acid such as acetic acid, propionic acid, butyric acid, caproic acid, caprylic acid, capric acid, lauric acid, myristic acid, palmitic acid or stearic acid; a linear unsaturated fatty acid such as palmitoleic acid, oleic acid, linoleic acid or linolenic acid; and a branched saturated fatty acid such as isobutyric acid, 2-ethylhexanoic acid, isostearic acid or multi-methyl branched isostearic acid. The fatty acid of the present invention is preferably caproic acid, caprylic acid, capric acid, lauric acid, myristic acid, palmitic acid or stearic acid, more preferably caproic acid, caprylic acid or capric acid having 6 to 10 carbon atoms, and most preferably caprylic acid (having 8 carbon atoms). These fatty acids having 2 to 18 carbon atoms may be used alone or in a combination of two or more thereof.

If the fatty acid constituting the polyglycerol fatty acid ester has a carbon number outside the range of 2 to 18 carbon atoms, this undesirably leads to a problem of safety such as irritation to skin or a problem of turbidity at a low temperature.

The polyglycerol fatty acid ester of the present invention is characterized by having a specific gravity at 20° C. of 0.96 to 1.15, more preferably 0.97 to 1.10, and even more preferably 0.97 to 1.03. A cosmetic containing the composition for cosmetics having a specific gravity within the above-specified range exhibits a high emulsion stability when being mixed with a hydrophilic solution such as water, even though having a low viscosity, for example a viscosity of 1500 mPa·s or less at 25° C., and is advantageous in terms of usability.

The polyglycerol fatty acid ester of the present invention is characterized by having a hydroxyl value of 15 mgKOH/g or less, preferably 10 mgKOH/g or less, and more preferably 4 mgKOH/g or less. When the hydroxyl value is 15 mgKOH/g or less, the composition for cosmetics exhibits no bitter taste and stickiness, and may be preferably used as a composition for cosmetics, such as lip rouge or lip gloss.

As it is also clear from the fact that with regard to the polyglycerol fatty acid ester of the present invention, as described above, the polyglycerol fatty acid ester preferably has a relatively low hydroxyl value, the esterification degree of the polyglycerol fatty acid ester is preferably high. Specifically, the esterification degree is preferably 95% or more, more preferably 97% or more, and even more preferably 98% or more. The polyglycerol fatty acid ester may be a full ester (esterification degree of 100%). When the esterification degree is 95% or more, this leads to inhibition of a feeling of resistance upon application of the composition for cosmetics, smoothness of a texture, inhibition of bitter taste, and provision of a very favorable usage sensation.

The polyglycerol fatty acid ester of the present invention preferably has a viscosity at 20° C. of 20 to 5000 mPa·s, more preferably 30 to 500 mPa·s, and most preferably 100 to 300 mPa·s. When the viscosity is within the above-specified range, this may lead to inhibition of a feeling of resistance upon application of the composition for cosmetics, smoothness of texture, and provision of a very favorable usage sensation. Further, as will be described hereinafter, a two-separate-layer-type cosmetic, or emulsion cosmetic containing the composition for cosmetics of the present invention contains a low-viscosity polyglycerol fatty acid ester as described above, and therefore even when a viscosity of the cosmetic is also low as above, an emulsion stability when being mixed with a hydrophilic solution such as water or a retention time of an emulsified state may become favorable.

The composition for cosmetics of the present invention may further contain a polyhydric alcohol and a non-ionic surfactant, in addition to the foregoing polyglycerol fatty acid ester. In particular, when the composition for cosmetics of the present invention is intended for an emulsion cosmetic such as emulsion, incorporation of a polyhydric alcohol and a non-ionic surfactant preferably contributes to improvements of water retention capacity, moisture-retaining property and emulsion stability.

The polyhydric alcohol in the present invention is not particularly limited, and examples thereof include 1,3-butylene glycol, 3-methyl-1,3-butylene glycol, 1,3-propanediol, dipropylene glycol, octanediol, hexanediol, glycerol, diglycerol, erythritol, pentaerythritol, dipentaerythritol, sorbitol, glucose, galactose, fructose, maltose, and trehalose.

Among these, the polyhydric alcohol of the present invention is preferably dipropylene glycol, octanediol, 1,3-propanediol or hexanediol and particularly preferably dipropylene glycol or 1,3-propanediol.

The polyhydric alcohol may be used alone or in a combination of two or more thereof.

The non-ionic surfactant in the present invention is not particularly limited and may be a lipophilic non-ionic surfactant or a hydrophilic non-ionic surfactant. Here, the non-ionic surfactant excludes the foregoing polyglycerol fatty acid ester which is an ester of polyglycerol having an average degree of polymerization of 4 to 100 with a fatty acid having 2 to 18 carbon atoms, has a hydroxyl value equal to or less than 15 mgKOH/g, and has a specific gravity at 20° C. of 0.96 to 1.15.

Examples of the lipophilic non-ionic surfactant include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; sucrose fatty acid esters; glycerol fatty acid esters such as glycerol mono-cottonseed oil fatty acid ester, glycerol monoerucate, glycerol sesquioleate, glycerol monostearate, glycerol α,α'-oleate pyroglutamate and glycerol monostearate; polyglycerol fatty acid esters; propylene glycol fatty acid esters such as propylene glycol monostearate; hydrogenated castor oil derivatives; and glycerol alkyl ethers.

Examples of the hydrophilic non-ionic surfactant include polyoxyethylene (POE) sorbitan fatty acid esters such as POE sorbitan monooleate, POE sorbitan monostearate, POE sorbitan monooleate and POE sorbitan tetraoleate; POE sorbitol fatty acid esters such as POE sorbitol monolaurate, POE sorbitol monooleate, POE sorbitol pentaoleate and POE sorbitol monostearate; POE glycerol fatty acid esters such as POE glycerol monostearate, POE glycerol monoisostearate and POE glycerol triisostearate; POE fatty acid esters such as POE monooleate, POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; Pluronics such as Pluronic; POE-POP alkyl ethers such as POE-POP cetyl ether, POE-POP 2-decyltetradecyl ether, POE-POP monobutyl ether, POE-POP hydrogenated lanolin ether and POE-POP glycerol ether; tetra-POE-tetra-POP ethylenediamine condensates such as Tetronic; POE castor oil/hydrogenated castor oil derivatives such as POE hydrogenated castor oil, POE hydrogenated castor oil monoisostearate, POE hydrogenated castor oil triisostearate, POE hydrogenated castor oil, POE hydrogenated castor oil monopyroglutamate monoisostearate diester and POE hydrogenated castor oil maleate; POE beeswax lanolin derivatives such as POE sorbitol beeswax; alkanolamides such as coconut oil fatty acid diethanolamide, lauric acid monoethanolamide and fatty acid isopropanolamides; POE propylene glycol fatty acid esters; POE alkylamines; POE fatty acid amides; sucrose fatty acid esters, POE nonylphenyl formaldehyde condensates, alkylethoxydimethylamine oxides; and trioleyl phosphoric acid.

Among these, the non-ionic surfactant of the present invention is preferably a hydrophilic non-ionic surfactant and particularly preferably POE-hydrogenated castor oil.

The foregoing non-ionic surfactants may be used alone or in a combination of two or more thereof.

When the composition for cosmetics of the present invention contains a polyhydric alcohol and a non-ionic surfactant, the content of the polyhydric alcohol is preferably in the range of 0.1 parts by mass to 50 parts by mass, more preferably 2 parts by mass to 50 parts by mass, and even more preferably 5 to 20 parts by mass, relative to 1 part by mass of the polyglycerol fatty acid ester. The content of the non-ionic surfactant is preferably in the range of 0.05 to 10 parts by mass and more preferably 0.1 to 5 parts by mass, relative to 1 part by mass of the polyglycerol fatty acid ester.

The composition for cosmetics of the present invention may further contain hydrogenated lecithin. The content of the hydrogenated lecithin is preferably in the range of 0.01 to 5 parts by mass and more preferably 0.05 to 1 parts by mass, relative to 1 part by mass of the polyglycerol fatty acid ester.

Use applications of the composition for cosmetics of the present invention are not particularly limited. The composition for cosmetics of the present invention may be preferably used for a skin care cosmetic, a bath cosmetic, a hair cosmetic, or a make-up cosmetic.

Examples of the skin care cosmetic include cleansing cosmetics such as cleansing oil, cleansing cream, cleansing paste (cleansing gel) and make-up remover; water-retaining and moisturizing cosmetics such as O/W emollient cream, W/O emollient cream, emulsions, emulsion lotion and beauty essence; massage cosmetics such as massage gel, massage oil and massage cream; and nail treatment cosmetics such as nail oil and nail cream.

The cleansing cosmetic containing the composition for cosmetics of the present invention is readily compatible with makeup dirt, is excellent in cleansing power, and exhibits a favorable post-wash texture. Further, when the cleansing cosmetic is a two-separate-layer-type cosmetic to be described later, it is advantageous in terms of usability because the retention time of an emulsified state when mixed with a hydrophilic solution such as water is long, and aesthetics of external appearance when not used is excellent because an aqueous phase and an oily phase are clearly separated after being used.

The water-retaining and moisturizing cosmetic containing the composition for cosmetics of the present invention has a moist feeling and a high water retention capacity, but exhibits no stickiness, thus giving an excellent usage sensation.

A massage cosmetic containing the composition for cosmetics of the present invention has good spreadability upon use thereof and a moist feeling, and exhibits no stickiness, thus giving an excellent usage sensation.

As the bath cosmetic, mention may be made of an emulsion bath agent or the like.

The emulsion bath agent containing the composition for cosmetics of the present invention is excellent in emulsion stability when mixed with a hydrophilic solution such as water and is therefore advantageous in terms of usability.

Examples of the hair cosmetic include a shampoo, a hair treatment, a hair conditioner and a hair dressing.

According to the hair cosmetic containing the composition for cosmetics in accordance with the present invention, combability of hair and manageability of hair are improved. Further, when the cleansing cosmetic is a two-separate-layer-type cosmetic to be described later, it is advantageous in terms of usability because the retention time of an emulsified state when mixed with a hydrophilic solution such as water is long, and aesthetics of external appearance when not used is excellent because an aqueous phase and an oily phase are clearly separated after being used.

Examples of the make-up cosmetic include an emulsion foundation, an emulsion eye shadow, an emulsion cheek cosmetic, a lip rouge and a lip gloss.

An emulsion foundation, an emulsion eye shadow, and an emulsion cheek cosmetic each containing the composition for cosmetics of the present invention have good spreadability upon use thereof and exhibit no stickiness, thus giving an excellent usage sensation.

A lip rouge and a lip gloss each containing the composition for cosmetics of the present invention are capable of inhibiting dryness of lips even though having good spreadability upon use thereof and exhibiting no stickiness, and are therefore excellent in a usage sensation. Further, these lip rouge and lip gloss containing the composition for cosmetics of the present invention are free from bitter taste and therefore may be used preferably for lips.

<<Cosmetic>>

The cosmetic of the present invention contains the foregoing composition for cosmetics.

Examples of the cosmetic of the present invention include, as described above, a skin care cosmetic, a bath cosmetic, a hair cosmetic and a make-up cosmetic.

The cosmetic of the present invention may be a two-separate-layer-type cosmetic, or an emulsion cosmetic. Examples of the two-separate-layer-type cosmetic include a two-separate-layer-type cleansing cosmetic and a two-separate-layer-type hair treatment. Examples of the emulsion cosmetic include an emulsion and an emulsion bath agent.

The cosmetic of the present invention may further appropriately contain various components commonly used in cosmetics, if necessary, within the range where the effect of the present invention is not impaired, in addition to the foregoing composition for cosmetics. Specific examples thereof include an oily component; a surfactant such as a non-ionic surfactant, an anionic surfactant, a cationic surfactant, an amphoteric surfactant or a natural surfactant; a powder component such as a moisturizer, a thickener, a preservative, a pigment or talc; a water-soluble polymer; an ultraviolet absorber; a sequestrant; a lower alcohol; saccharides; a synthetic resin emulsion; salts; a pH adjuster; a plant extract; an antioxidant; a dye; and perfume. These components may be used alone or in a combination of two or more thereof.

Examples of the oily component include a hydrocarbon oil, a synthetic ester oil, animal/vegetable oil, a silicon oil, a higher fatty acid, and a higher alcohol. These components may be used alone or in a combination of two or more thereof. These components may be liquid, semi-solid or solid at room temperature and may be used without particular limitation.

Examples of the hydrocarbon oil include light liquid isoparaffin, liquid paraffin, polydecene, hydrogenated polydecene, polyisobutene, hydrogenated polyisobutene, squalane, squalane paraffin wax, α-olefin oligomer, ozocerite, pristane, ceresin, Vaseline, microcrystalline wax, paraffin wax, and polyethylene wax.

Examples of the synthetic ester oil include 2-pentylnonyl hexanoate, 2-hexyldecyl hexanoate, 2-heptylundecyl hexanoate, 2-octyldodecyl hexanoate, isostearyl hexanoate, 2-butyloctyl octanoate, isotrideceyl octanoate, 2-pentylnonyl octanoate, 2-hexyldecyl octanoate, 2-heptylundecyl octanoate, 2-octyldodecyl octanoate, isostearyl octanoate, 2-propylheptyl decanoate, 2-butyloctyl decanoate, isotridecyl decanoate, 2-pentylnonyl decanoate, 2-hexyldecyl decanoate, 2-heptylundecyl decanoate, 2-octyldodecyl decanoate, isostearyl decanoate, 2-propylheptyl laurate, isononyl laurate, 2-butyloctyl laurate, isotridecyl laurate, isotridecyl laurate, 2-pentylnonyl laurate, 2-hexyldecyl laurate, 2-heptylundecyl laurate, 2-octyldodecyl laurate, isotridecyl laurate, isostearyl laurate, isopropyl myristate, 2-ethylhexyl myristate, isononyl myristate, 2-propylheptyl myristate, 2-butyloctyl myristate, isotridecyl myristate, 2-pentylnonyl myristate, 2-hexyldecyl myristate, 2-heptylundecyl myristate, 2-octyldodecyl myristate, isostearyl myristate, isobutyl palmitate, 2-ethylhexyl palmitate, isononyl palmitate, 2-propylheptyl palmitate, 2-butyloctyl palmitate, isotridecyl palmitate, 2-pentylnonyl palmitate, 2-hexyldecyl palmitate, 2-heptylundecyl palmitate, 2-octyldodecyl palmitate, isostearyl palmitate, isopropyl stearate, isobutyl stearate, 2-ethylhexyl stearate, isononyl stearate, 2-propylheptyl stearate, 2-butyloctyl stearate, isotridecyl stearate, 2-pentylnonyl stearate, 2-hexyldecyl stearate, 2-heptylundecyl stearate, 2-octyldodecyl stearate, isostearyl stearate, isopropyl behenate, isobutyl behenate, 2-ethylhexyl behenate, isononyl behenate, 2-propylheptyl behenate, 2-butyloctyl behenate, isotridecyl behenate, 2-pentylnonyl behenate, 2-hexyldecyl behenate, 2-heptylundecyl behenate, 2-octyldodecyl behenate, isostearyl behenate, dodecyl 2-ethylhexanoate, myristyl 2-ethylhexanoate, palmityl 2-ethylhexanoate, stearyl 2-ethylhexanoate, 2-propylheptyl 2-ethylhexanoate, 2-butyloctyl 2-ethylhexanoate, isotridecyl 2-ethylhexanoate, 2-pentylnonyl 2-ethylhexanoate, 2-hexyldecyl 2-ethylhexanoate, 2-heptylundecyl 2-ethylhexanoate, 2-octyldodecyl 2-ethylhexanoate, isostearyl 2-ethylhexanoate, isononyl isononanoate, dodecyl isononanoate, myristyl isononanoate, palmityl isononanoate, stearyl isononanoate, behenyl isononanoate, 2-butyloctyl isononanoate, isotridecyl isononanoate, 2-pentylnonyl isononanoate, 2-hexyldecyl isononanoate, 2-heptylundecyl isononanoate, 2-octyldodecyl isononanoate, isostearyl isononanoate, decyl isodecanoate, undecyl isodecanoate, dodecyl isodecanoate, myristyl isodecanoate, palmityl isodecanoate, stearyl isodecanoate, 2-propylheptyl isodecanoate, 2-butyloctyl isodecanoate, isotridecyl isodecanoate, 2-pentylnonyl isodecanoate, 2-hexyldecyl isodecanoate, 2-heptylundecyl isodecanoate, 2-octyldodecyl isodecanoate, isostearyl isodecanoate, heptyl isotridecanoate, octyl isotridecanoate, nonyl isotridecanoate, decyl isotridecanoate, undecyl isotridecanoate, dodecyl isotridecanoate, myristyl isotridecanoate, palmityl isotridecanoate, stearyl isotridecanoate, isopropyl isotridecanoate, isobutyl isotridecanoate, 2-ethylhexyl isotridecanoate, 2-propylheptyl isotridecanoate, 2-butyloctyl isotridecanoate, isotridecyl isotridecanoate, 2-pentylnonyl isotridecanoate, 2-hexyldecyl isotridecanoate, 2-heptylundecyl isotridecanoate, 2-octyldodecyl isotridecanoate, isostearyl isotridecanoate, propyl isostearate, butyl isostearate, pentyl isostearate, hexyl isostearate, heptyl isostearate, octyl isostearate, nonyl isostearate, decyl isostearate, undecyl isostearate, dodecyl isostearate, myristyl isostearate, palmityl isostearate, stearyl isostearate, isopropyl isostearate, isobutyl isostearate, 2-ethylhexyl isostearate, 2-propylheptyl isostearate, 2-butyloctyl isostearate, isotridecyl isostearate, 2-pentylnonyl isostearate, 2-hexyldecyl isostearate, 2-heptylundecyl isostearate, 2-octyldodecyl isostearate, isostearyl isostearate, propyl oleate, butyl oleate, pentyl oleate, hexyl oleate, heptyl oleate, octyl oleate, nonyl oleate, decyl oleate, undecyl oleate, dodecyl oleate, myristyl oleate, palmityl oleate, stearyl oleate, isopropyl oleate, isobutyl oleate, 2-ethylhexyl oleate, 2-propylheptyl oleate, 2-butyloctyl oleate, isotridecyl oleate, 2-pentylnonyl oleate, 2-hexyldecyl oleate, 2-heptylundecyl oleate, 2-octyldodecyl oleate, isostearyl oleate, isononyl isononanoate, isodecyl isononanoate, isopropyl myristate, isopropyl palmitate, butyl stearate, hexyl laurate, myristyl myristate, hexyldecyl dimethyloctanoate, cetyl lactate, myristyl lactate, octyldodecyl lactate, lanolin acetate, cholesteryl 12-hydroxystearate, phytosteryl 12-hydroxystearate, phytosteryl oleate, ethylene glycol di-2-ethylhexanoate, dipentaerythritol fatty acid ester, alkyl glycol monoisostearate, neopentyl glycol diethylhexanoate, neopentyl glycol dicaproate, glyceryl di-2-heptylundecanoate, pentaerythritol tetra-2-ethylhexanoate, pentaerythritol tetraisostearate, glyceryl tri-2-ethylhexanoate, glyceryl tri(caprylate/caproate), glyceryl triisostearate, glyceryl tri(caprylate/caproate/myristate/stearate), glyceryl trimyristate, glyceryl tricaprylate, glyceryl tricaproate, glyceryl tri-2-heptylundecanoate, trimethylolpropane triisostearate, trimethylolpropane tri-2-ethylhexanoate, ditrimethylolpropane oligoester (isostearate/sebacate), erythrityl triethylhexanoate, dipentaerythrityl tri-polyhydroxystearate, trehalose isostearate esters, dipentaerythrityl pentaisostearate, diglyceryl triisostearate, diglyceryl tetraisostearate, diisostearyl malate, castor oil fatty acid methyl ester, isopropyl lanolin fatty acid, acetoglyceride, diisobutyl adipate, glyceryl (ethylhexanoate/stearate/adipate), diglyceryl oligoester (hexyldecanoate/sebacate), N-lauroyl-L-glutamic acid-2-octyldodecyl ester, di-2-heptylundecyl adipate, hexyl laurate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, glycerol triisopalmitate, ethyl acetate, butyl acetate, triethyl citrate, glyceryl tri(behenate/isostearate/eicosanedioate), glyceryl (behenate/eicosanedioate), and polyglyceryl (behenate/eicosanedioate).

Examples of the animal/vegetable oil include avocado oil, camellia oil, turtle oil, macadamia nut oil, corn oil, sunflower oil, mink oil, olive oil, rapeseed oil, egg yolk oil, sesame oil, persic oil, wheat germ oil, sasanqua oil, castor oil, linseed oil, safflower oil, grapeseed oil, cottonseed oil, perilla oil, soybean oil, peanut oil, tea seed oil, Japanese nutmeg oil, rice bran oil, *Aleurites fordii* oil, Japanese tung oil, jojoba oil, germ oil, evening primrose oil, cacao fat, coconut oil, beef tallow, mutton tallow, horse tallow, palm kernel oil, lard, beef bone fat, tree wax kernel oil, hoof oil, tree wax, hardened coconut oil, hardened palm oil, hardened beef tallow, hardened oil, hydrogenated castor oil, beeswax, candelilla wax, cotton wax, carnauba wax, bayberry wax, *Ericerus pela* wax, spermaceti, montan wax, bran wax, kapok wax, sugar cane wax, lanolin, liquid lanolin, reduced lanolin, hardened lanolin, jojoba wax, and shellac wax.

Examples of the silicon oil include chain polysiloxanes such as dimethyl polysiloxane, methylphenyl polysiloxane and methylhydrogen polysiloxane; cyclic polysiloxanes such as octamethylcyclotetrasiloxane, decamethylcyclopentasiloxane, dodecamethylcyclohexasiloxane and tetrahydrotetramethylcyclotetrasiloxane; and polyoxyethylene polyalkyl siloxane.

Examples of the higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA) and docosahexaenoic acid (DHA).

Examples of the higher alcohol include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyl tetra decynol, lanolin alcohol, cholesterol, phytosterol, hexyl dodecanol, isostearyl alcohol and octyl dodecanol.

Examples of the non-ionic surfactant are the same as those described hereinbefore.

Examples of the anionic surfactant include fatty-acid soaps such as substrates for soap, sodium laurate and sodium palmitate; salts of higher alkyl sulfuric ester such as sodium lauryl sulfate and potassium lauryl sulfate; salts of alkyl ether sulfuric ester such as polyoxyethylene (POE)-triethanolamine lauryl sulfate and POE-sodium lauryl sulfate; N-acylsarcosine acids such as sodium lauroyl sarcosine; higher fatty acid amide sulfonates such as sodium N-myristoyl-N-methyl taurate, sodium palm oil fatty acid methyl tauride and sodium lauryl methyl tauride; salts of phosphoric ester such as sodium POE-oleyl ether phosphate and POE-stearyl ether phosphoric acid; sulfosuccinates such as sodium di-2-ethylhexyl sulfosuccinate, sodium monolauroyl monoethanolamide polyoxyethylene sulfosuccinate and sodium lauryl polypropylene glycol sulfosuccinate; alkylbenzene sulfonates such as sodium linear dodecyl benzenesulfonate, linear triethanolamine dodecylbenzenesulfonate and linear dodecylbenzenesulfonic acid; N-acylglutamates such as monosodium N-lauroyl glutamate, disodium N-stearoyl glutamate and monosodium N-myristoyl-L-glutamate; higher fatty acid ester sulfates such as hardened palm oil fatty acid glycerin sodium sulfate; sulfated oils such as Turky red oil; POE-alkylether carboxylic acids; POE-alkylallyl ether carboxylate; α-olefin sulfonate; higher fatty acid ester sulfonate; salts of secondary alcohol sulfate esters; salts of higher fatty acid alkylol amide sulfates esters; sodium lauroyl monoethanolamide succinate; ditriethanolamine salts of N-palmitoyl aspartic acid; and sodium caseinate. These anionic surfactants may be used alone or in a combination of two or more thereof.

Examples of the cationic surfactant include alkyltrimethyl ammonium salts such as stearyl trimethyl ammonium chloride and lauryl trimethyl ammonium chloride; dialkyl dimethyl ammonium salts such as distearyl dimethyl ammonium chloride; alkylpyridinium salts such as poly(N,N'-dimethyl-3,5-methylene piperidinium) chloride and cetylpyridinium chloride; alkyl quaternary ammonium salts; alkyl dimethyl benzyl ammonium salts; alkyl isoquinolinium salts; dialkyl morphonium salts; POE-alkylamine; alkylamine salts; polyamine fatty acid derivatives; amyl alcohol fatty acid derivatives; benzalkonium chloride; and benzethonium chloride. These cationic surfactants may be used alone or in a combination of two or more thereof.

Examples of the amphoteric surfactant include imidazoline amphoteric surfactants such as sodium 2-undecyl-N,N,N-(hydroxyethyl carboxymethyl)-2-imidazoline and salts of disodium 2-cocoyl-2-imidazolinium hydroxide-1-carboxyethyloxy; and betaine amphoteric surfactants such as 2-heptadecyl-N-carboxymethyl-N-hydroxyethyl imidazolinium betaine, lauryl dimethylamino acetic acid betaine, alkyl betaine, amido betaine and sulfobetaine. These amphoteric surfactants may be used alone or in a combination of two or more thereof.

Examples of the natural surfactant include lecithins such as soybean phospholipids, hydrogenated soybean phospholipids, egg yolk phospholipids and hydrogenated egg yolk phospholipids; and soybean saponins. These natural surfactants may be used alone or in a combination of two or more thereof.

Examples of the moisturizer include polyethylene glycol (PEG1500), propylene glycol, 1,3-propanediol, 3-methyl-1,3-butanediol, glycerol, 1,3-butylene glycol, xylitol, sorbitol, maltitol, chondroitin sulfuric acid, hyaluronic acid, mucoitin sulfuric acid, *Trichosanthis semen* acid, atelocollagen, cholesteryl-12-hydroxy stearate, sodium lactate, urea, bile salt, dl-pyrrolidone carboxylate, short-chain soluble collagen, diglycerin (EO) PO adducts, *Rosa roxburghii* extracts, yarrow extracts and melilot extracts. These moisturizers may be used alone or in a combination of two or more thereof.

Examples of the thickener include gum arabic, carrageenan, Karaya gum, gum tragacanth, carob gum, quince seed (marmelo), casein, dextrin, gelatin, sodium pectinate, sodium alginate, methylcellulose, ethylcellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, magnesium aluminum silicate, bentonite, hectorite, quaternary ammonium salt-based cation-modified bentonite, quaternary ammonium salt-based cation-modified hectorite, and decaglycerin fatty acid ester eicosadioate condensate. These thickeners may be used alone or in a combination of two or more thereof.

Examples of the preservative include methylparaben, ethylparaben and butylparaben. These preservatives may be used alone or in a combination of two or more thereof.

Examples of the pigment include inorganic white pigments such as titanium dioxide and zinc oxide (including fine particles of titanium dioxide or zinc oxide which are used as ultraviolet-scattering agents and surface-coated inorganic white pigments through coating the surfaces of the particles with fatty acid soap such as aluminum stearate or zinc palmitate; fatty acids such as stearic acid, myristic acid or palmitic acid; or fatty acid esters such as dextrin palmitate); inorganic red pigments such as iron oxide (bengara) and iron titanate; inorganic brown pigments such as γ-iron oxide; inorganic yellow pigments such as yellow iron oxide and yellow ocher; inorganic black pigments such as black iron oxide, carbon black, and titanium suboxide; inorganic violet pigments such as mango violet and cobalt violet; inorganic green pigments such as chromium oxide, chromium hydroxide, and cobalt titanate; inorganic blue pigments such as ultramarine blue and iron blue; pearl pigments such as titanium oxide-coated mica, titanium oxide-coated bismuth oxychloride, titanium oxide-coated talc, colored titanium oxide-coated mica, bismuth oxychloride, and argentine film; metal powder pigments such as aluminum powder and copper powder; organic pigments such as Red Nos. 201, 202, 204, 205, 220, 226, 228, and 405, Orange Nos. 203 and 204, Yellow Nos. 205 and 401, and Blue No. 404; and organic pigments such as zirconium, barium, and aluminum lakes of Red Nos. 3, 104, 106, 227, 230, 401, and 505, Orange No. 205, Yellow Nos. 4, 5, 202, and 203, Green No. 3, and Blue No. 1. These pigments may be used alone or in a combination of two or more thereof.

Examples of the powder component include inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal salts of tungstic acid, magnesium, silica, zeolite, barium sulfate, calcined calcium sulfate (calcined gypsum), calcium phosphate, fluorapatite, hydroxyapatite, ceramic powder, metallic soaps (such as zinc myristate, calcium palmitate and aluminum stearate) and boron nitride; and organic powders such as polyamide resin powder (nylon powder), polyethylene powder, poly(methyl methacrylate) powder, polystyrene powder, powder of a copolymer resin of styrene and acrylic acid, benzoguanamine resin powder, poly(ethylene tetrafluoride) powder and cellulose powder. These powder components may be used alone or in a combination of two or more thereof.

The water-soluble polymer may be natural, synthetic, partially synthetic (semi-synthetic), or inorganic, and an example thereof is preferably a carbomer or the like.

Examples of the ultraviolet absorber include benzoic acid ultraviolet absorbers such as p-aminobenzoic acid (hereinafter, abbreviated as "PABA"), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester; anthranilic acid ultraviolet absorbers such as homomethyl-N-acetyl anthranilate; salicylic acid ultraviolet absorbers such as amyl salicylate, menthyl salicylate, homomethyl salicylate, octyl salicylate, phenyl salicylate, benzyl salicylate, and p-isopropanol phenyl salicylate; cinnamic acid ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, and glycerylmono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethyl hexyl-4'-phenylbenzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; urocanic acid; ethyl urocanate ester; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; dibenzalazine; dianisoylmethane; 4-methoxy-4'-t-butyldibenzoylmethane; 5-(3,3-dimethyl-2-norbornylidene)-3-pentan-2-one; 2,4,6-trianilino-p-(carbo-2'-ethylhexyl-1'-oxy)-1,3,5-triazine; and 4-tert-butyl-4'-methoxydibenzoylmethane. These ultraviolet absorbers may be used alone or in a combination of two or more thereof.

Examples of the sequestrant include disodium edetate, edetic acid salts, and hydroxyethane diphosphonate. These sequestrants may be used alone or in a combination of two or more thereof.

Examples of the lower alcohol include methanol, ethanol, propanol, isopropanol, isobutyl alcohol and t-butyl alcohol.

Examples of the saccharide include monosaccharides, oligosaccharides and polysaccharides.

Examples of the synthetic resin emulsion include alkyl acrylate copolymer emulsion, alkyl methacrylate polymer emulsion, alkyl acrylate copolymer emulsion, alkyl methacrylate copolymer emulsion, acrylic acid/alkyl acrylate copolymer emulsion, methacrylic acid/alkyl methacrylate copolymer emulsion, alkyl acrylate/styrene copolymer emulsion, alkyl methacrylate/styrene copolymer emulsion, vinyl acetate polymer emulsion, polyvinyl acetate emulsion, vinyl acetate-containing copolymer emulsion, vinyl pyrrolidone/styrene copolymer emulsion, and silicone-containing copolymer emulsion. These synthetic resin emulsions may be used alone or in a combination of two or more thereof.

Examples of the salt include sodium chloride, potassium chloride, sodium sulfate and magnesium sulfate.

Examples of the pH adjuster include edetic acid, disodium edetate, citric acid, sodium citrate, sodium hydroxide, potassium hydroxide, and triethanolamine. These pH adjusters may be used alone or in a combination of two or more thereof.

Examples of the plant extract include *Aloe vera*, witch hazel, *Hamamelis*, cucumber, lemon, lavender and rose extracts.

Examples of the antioxidant include vitamin C, its derivatives, and salts thereof; tocopherol, its derivatives, and salts thereof; dibutylhydroxytoluene; butylhydroxyanisole; and gallic acid ester. These antioxidants may be used alone or in a combination of two or more thereof.

Examples of the dye include chlorophyll and β-carotene. These dyes may be used alone or in a combination of two or more thereof.

Examples of the perfume include plant perfumes such as rose oil, jasmine oil, and lavender oil; and synthetic perfumes such as limonene, citral, linalool, and eugenol. These perfumes may be used alone or in a combination of two or more thereof.

<<Method for Producing an Oil-in-Water Emulsion Cosmetic>>

The oil-in-water (O/W) emulsion cosmetic of the present invention is prepared by mixing the composition for cosmetics of the present invention with a hydrophilic solution and emulsifying the mixture.

The hydrophilic solution is not particularly limited as long as the effect of the present invention is not impaired, but an example thereof is preferably water.

Examples of the water that can be used in the present invention include purified water such as distilled water or ion-exchange water, water obtained from fruits or flowers, and water obtained by purifying seawater. These waters may be used alone or in a combination of two or more thereof.

Further, in the hydrophilic solution, if necessary, known auxiliary components may be dissolved or dispersed in advance. In this case, an oil-in-water emulsion cosmetic may be prepared by adding the composition for cosmetics of the present invention to the hydrophilic solution in which auxiliary components are dissolved or dispersed in advance; or alternatively an oil-in-water emulsion cosmetic may be prepared by adding the hydrophilic solution having auxiliary components dissolved or dispersed in advance to the composition for cosmetics of the present invention.

The auxiliary component in the present invention is preferably a surfactant and/or a water-soluble thickener.

The surfactant is not particularly limited as long as it is commonly used in cosmetics, and examples thereof preferably include polyglycerol fatty acid esters such as polyglyceryl-2 oleate, polyglyceryl-10 oleate, polyglyceryl-10 stearate, polyglyceryl-10 distearate and polyglyceryl-10 myristate, and hydrogenated lecithin. These surfactants may be used alone or in a combination of two or more thereof. The content of the surfactant in the oil-in-water emulsion cosmetic is preferably in the range of 0.001 to 20% by mass, more preferably 0.01 to 10% by mass, and most preferably 0.05 to 5% by mass.

Examples of the water-soluble thickener are the same as those described for the thickener hereinbefore.

Further, the oil-in-water emulsion cosmetic in accordance with the present invention may also contain known component(s) for use in a usual cosmetic preparation, for example, a moisturizer, a powder component, an ultraviolet absorber, an antioxidant, saccharides, a plant extract, a preservative, a perfume, a pH adjuster, and a dye, within a range where the effect of the present invention is not impaired. Examples of these known components are the same as those described hereinbefore.

The viscosity at 25° C. of the oil-in-water emulsion cosmetic in accordance with the present invention is preferably in the range of 50 to 5000 mPa·s, more preferably 100 to 4000 mPa·s, and most preferably 500 to 3000 mPa·s.

There is no particular limitation on the method of producing an oil-in-water (O/W) emulsion cosmetic by adding the composition for cosmetics of the present invention to the hydrophilic solution, as long as the effect of the present invention is not impaired, and the components in the hydrophilic solution and the composition for cosmetics of the present invention are not impaired. For example, preferred is a method of producing an oil-in-water (O/W) emulsion cosmetic by slowly adding a lipophilic solution containing the composition for cosmetics of the present invention heated to a temperature of 60 to 90° C. to the hydrophilic solution heated to a temperature of 60 to 90° C., under stirring, thereby preparing a mixed solution, and cooling the mixed solution under stirring.

Here, the content of the hydrophilic solution is preferably in the range of 1 to 100 parts by mass and more preferably 1 to 20 parts by mass, relative to 1 part by mass of the lipophilic solution containing the composition for cosmetics of the present invention.

Incidentally, as a method of adding to the cosmetic an component for which heating is undesirable among the foregoing auxiliary components, preferred is a method of adding the relevant auxiliary component without performing dissolution or dispersion thereof in advance in the aqueous solution, at a point at which the mixed solution is cooled to an appropriate temperature, in the course of cooling the temperature of the mixed solution to room temperature.

The thus-prepared oil-in-water emulsion cosmetic may be preferably used as a lotion, a beauty essence, an emulsion, a bath additive, or the like.

<<Two-Separate-Layer-Type Cosmetic Packaged in Transparent or Translucent Container>>

The two-separate-layer-type cosmetic of the present invention packaged in a transparent or translucent container may be obtained by accommodating a two-separate-layer-type cosmetic containing the composition for cosmetics of the present invention and water in a transparent or translucent container.

The two-separate-layer-type cosmetic may be prepared in the same manner as in the method for producing an oil-in-water emulsion cosmetic.

The transparent or translucent container is not particularly limited as long as the two-separate-layer-type cosmetic is preferably stored through the accommodation of the cosmetic therein. The container may be made of a known material such as glass, polyethylene (PE), polyethylene terephthalate (PET) or polypropylene (PP).

Through the accommodation of the two-separate-layer-type cosmetic in a transparent or translucent container, the corresponding cosmetic may be used with the confirmation of separation and emulsified state, and the corresponding cosmetic may be used with enjoyment by observing changes in the state of the cosmetic.

EXAMPLES

The present invention will now be described in more detail with reference to Examples. However, it is apparent that the present invention is not limited to the following Examples.

Synthesis Example 1

Preparation of polyglycerol fatty acid ester A

A 1 L four-necked flask was charged with 194.2 g (0.35 mol) of commercially available polyglycerol (Polyglycerol #500, manufactured by Sakamoto Yakuhin Kogyo Co., Ltd., water content: approximately 10%) having an average degree of polymerization of 6, and 405.8 g (2.81 mol) of caprylic acid and 50 ml of xylene was added thereto. The mixture was heated and stirred under a nitrogen stream at a temperature of 230° C., followed by reaction for 18 hours while removing water being distilled together with refluxing xylene, using a Dean-Stark water separator.

The resulting reaction mixture was cooled, followed by complete distillation of xylene under reduced pressure (5 mmHg) at a temperature of 130° C., and cooled again. A decolorization treatment was carried out by adding 6 g of activated clay and 6 g of activated carbon, and stirring the mixture under reduced pressure (5 mmHg) at a temperature of 105° C. for 1 hour.

After the reaction mixture subjected to the decolorization treatment was cooled, the activated clay and activated carbon were removed by filtration to obtain a decolorization reaction mixture. The resulting decolorization reaction mixture was treated by blowing of steam under reduced pressure (2 mmHg) at a temperature of 220° C. for 1 hour, thereby removing the unreacted fatty acid. 450.2 g of desired polyglycerol fatty acid ester A (having a specific gravity at 20° C. of 0.997 as measured according to Japanese Standards of Food Additives, $8^{th}$ edition, B-32, $4^{th}$ method, a viscosity at 20° C. of 196 mPa·s, and a hydroxyl value of 2.0) was obtained. The yield of polyglycerol caprylate was approximately 85%.

Synthesis Example 2

Preparation of Polyglycerol Fatty Acid Ester B

A 1 L four-necked flask was charged with 151.6 g (0.20 mol) of commercially available polyglycerol (Polyglycerol #750, manufactured by Sakamoto Yakuhin Kogyo Co., Ltd., water content: approximately 10%) having an average degree of polymerization of 10, and 380.7 g (2.64 mol) of caprylic acid, and 50 ml of xylene was added thereto. The mixture was heated and stirred under a nitrogen stream at a temperature of 230° C., followed by reaction for 18 hours while removing water being distilled together with refluxing xylene, using a Dean-Stark water separator.

The resulting reaction mixture was cooled, followed by complete distillation of xylene under reduced pressure (5 mmHg) at a temperature of 130° C., and cooled again. A decolorization treatment was carried out by adding 6 g of activated clay and 6 g of activated carbon, and stirring the mixture under reduced pressure (5 mmHg) at a temperature of 105° C. for 1 hour.

After the reaction mixture subjected to the decolorization treatment was cooled, the activated clay and activated carbon were removed by filtration to obtain a decolorization reaction mixture. The resulting decolorization reaction mixture was treated by blowing of steam under reduced pressure (2 mmHg) at a temperature of 220° C. for 1 hour, thereby removing the unreacted fatty acid. 400.0 g of desired polyglycerol fatty acid ester B (having a specific gravity at 20° C. of 1.000, a viscosity at 20° C. of 284 mPa·s, and a hydroxyl value of 2.1) was obtained. The yield of polyglycerol caprylate was approximately 88%.

Example 1 and Comparative Examples 1 to 3

Measurement of Friction Coefficient

In Example 1, the polyglycerol fatty acid ester A obtained in Synthesis Example 1 was used as the composition for cosmetics of the present invention and a friction coefficient thereof was measured.

For Comparative Examples 1 to 3, the compounds used were as follows: Comparative Example 1 triethylhexanoin (manufactured by The Nisshin OilliO Group, Ltd.), Comparative Example 2: squalane (manufactured by Wako Pure Chemical Industries, Ltd.), and Comparative Example 3: isononyl isononanoate (manufactured by The Nisshin OilliO Group, Ltd.).

The friction coefficient was measured by such a way that: 5 µL of each composition for cosmetics was applied onto the surface of an artificial leather (Product Name: Supplale, manufactured by Idemitsu Technofine Co., Ltd.), and the applied surface was measured with respect to the friction coefficient and the change in the value of the friction coefficient, by using a friction tester (Model number: TL201Ts, manufactured by Trinity-Lab Co., Ltd.) with a load of 100 g. The results are shown in Table 1.

TABLE 1

|  | Example 1 | Comparative Example 1 | Comparative Example 2 | Comparative Example 3 |
| --- | --- | --- | --- | --- |
| Friction coefficient | 0.117 | 0.162 | 0.158 | 0.249 |
| Change in friction coefficient | 0.0036 | 0.0050 | 0.0064 | 0.0063 |

From the results of Table 1, it is clear that the composition for cosmetics of Example 1 exhibits a smaller friction coefficient and a lower change in friction coefficient, as compared to those of the compositions for cosmetics Comparative Examples 1 to 3. That is, it can be seen that the composition for cosmetics containing the polyglycerol fatty acid ester A in accordance with the present invention exhibits a lower feeling of resistance and a smooth texture, as compared to the compositions for cosmetics of Comparative Examples 1 to 3. It is apparent that when the composition for cosmetics containing the polyglycerol fatty acid ester A in accordance with the present invention is used as a substitute for the compositions for cosmetics of Comparative Examples 1 to 3, in terms of use thereof as a skin care cosmetic such as a massage oil, a make-up cosmetic such as lip rouge, and a hair cosmetic such as hair conditioner, the composition for cosmetics gives a smooth texture through a cosmetic.

Example 2 and Comparative Examples 4 to 5

Emulsion

Component A shown in Table 2 was mixed and heated to 80° C., thereby preparing a polyhydric alcohol phase. Meanwhile, Component B including polyglycerol fatty acid ester A as the composition for cosmetics of the present invention was heated to 80° C. to prepare an oily phase. The oily phase heated to the same temperature of 80° C. was added to the polyhydric alcohol phase heated to 80° C. under stirring with a dispersion mixer. Then, Component C heated and dissolved at 80° C. was added thereto, and the mixture was cooled to room temperature, thereby preparing an emulsion.

The resulting emulsion was evaluated according to the following evaluation method and evaluation criteria.

[Measurement of Average Particle Diameter of Emulsion Particles]

The average particle diameter of the prepared emulsion was measured with a particle size distribution analyzer (LA-300, manufactured by Horiba Ltd.).

[Evaluation Method and Evaluation Criteria for Emulsion Stability of Emulsion]

Each of the thus-prepared emulsions was centrifuged using a centrifuge (Model No.: 6800, manufactured by Kubota Corp.) at 5000 rpm for 15 minutes, followed by examination of the external appearance thereof. The emulsion stability was evaluated according to the following evaluation criteria. The emulsion with a grade of C or higher was rated as having passed the test.

Evaluation Criteria of Emulsion Stability

A: No separation

B: Little separation

C: Slight separation

D: Separation

E: Complete separation.

[Evaluation of Usage Sensation]

10 subjects were allowed to use the thus-prepared emulsions, and sensory evaluation for moist feeling and stickiness was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the emulsion with a grade of C or higher was rated as having passed the test.

Evaluation Criteria for Moist Feeling and Stickiness

A: Total score is 18 points or more.

B: Total score is 15 points or more and less than 18 points.

C: Total score is 12 points or more and less than 15 points.

D: Total score is 10 points or more and less than 12 points.

E: Total score is less than 10 points.

TABLE 2

(unit: wt %)

| Component | | Example 2 | Comparative Example 4 | Comparative Example 5 |
|---|---|---|---|---|
| A | Hydrogenated lecithin[1] | 0.1 | 0.1 | 0.1 |
| | Polyglyceryl-10 myristate[2] | 0.1 | 0.1 | 0.1 |
| | Glycerol | 3.0 | 3.0 | 3.0 |
| | 1,3-propanediol | 1.0 | 1.0 | 1.0 |
| | Water | 0.3 | 0.3 | 0.3 |
| B | Polyglycerol fatty acid ester A | 5.5 | — | — |
| | Squalane | — | 5.5 | — |
| | Glyceryl tri(caprylate/caproate) | — | — | 5.5 |
| C | 1,3-propanediol | 19.0 | 19.0 | 19.0 |
| | Water | 70.6 | 70.6 | 70.6 |
| | Quince seed[3] | 0.4 | 0.4 | 0.4 |
| Evaluation | Average particle diameter of emulsion particles (μm) | 1.08 | 1.03 | 1.73 |
| | Emulsion stability | B | E | E |
| | Moist feeling | B | B | C |
| | Stickiness | A | D | C |

[1]Basis LS-60HR, manufactured by The Nisshin OilliO Group, Ltd.
[2]Sunsoft Q-14S, manufactured by Taiyo Kagaku Co., Ltd.
[3]Quince seed powder, manufactured by Taiyo Kagaku Co., Ltd.

From the results of Table 2, it is clear that the emulsion of Example 2 in accordance with the present invention is excellent in emulsion stability and a usage sensation, as compared to the emulsions of Comparative Examples 4 and 5.

Example 3 and Comparative Example 6

O/W Emulsion Emollient Cream

Polyglycerol fatty acid ester A is used as the composition for cosmetics of the present invention, and Component A and Component B shown in Table 3 were mixed and heated to 80° C., thereby preparing an oily phase. Meanwhile, Component C was heated and dissolved at 80° C. to prepare an aqueous phase. The aqueous phase heated to the same temperature of 80° C. was added to the oily phase heated to 80° C. under stirring with a dispersion mixer, followed by cooling to 40° C. Thereafter, Component D and Component E were added thereto, followed by stirring. The mixture was cooled to room temperature to prepare an O/W emulsion emollient cream.

The resulting O/W emulsion emollient cream was evaluated according to the following evaluation method and evaluation criteria.

[Evaluation of Usage Sensation]

10 subjects were allowed to use the thus-prepared O/W emulsion emollient creams, and sensory evaluation for moist feeling and stickiness was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the cream with a grade of C or higher was rated as having passed the test.

Evaluation Criteria for Moist Feeling and Stickiness
A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 3

(unit: wt %)

| Component | | Example 3 | Comparative Example 6 |
|---|---|---|---|
| A | Polyglycerol fatty acid ester A | 5.0 | — |
| | Squalane | — | 5.0 |
| B | Dipentaerythrityl hexa(hydroxystearate/stearate/rosinate)[1] | 2.0 | 2.0 |
| | Triethyl hexanoin[2] | 6.0 | 6.0 |
| | Hydrogenated lecithin[3] | 0.2 | 0.2 |
| | Sorbitan sesquioleate[4] | 0.1 | 0.1 |
| | Microcrystalline wax | 3.0 | 3.0 |
| | Cetyl alcohol | 2.0 | 2.0 |
| | Glyceryl stearate(SE)[6] | 1.5 | 1.5 |
| | Polysorbate 80[7] | 0.1 | 0.1 |
| C | 1,3-BG | 16.0 | 16.0 |
| | Glycerol | 10.0 | 10.0 |
| | Sodium stearoyl methyl tauride[8] | 0.3 | 0.3 |
| | Methylparaben | 0.1 | 0.1 |
| | Water | 28.4 | 28.4 |
| D | 1% sodium hydroxide aqueous solution | 5.2 | 5.2 |
| E | 1% carbomer aqueous solution | 20.0 | 20.0 |
| Evaluation | Moist feeling | A | A |
| | Stickiness | B | D |

[1]Cosmol 168ARV, manufactured by The Nisshin OilliO Group, Ltd.
[2]T.I.O, manufactured by The Nisshin OilliO Group, Ltd.
[3]Basis LS-60HR, manufactured by The Nisshin OilliO Group, Ltd.
[4]Cosmol 82, manufactured by The Nisshin OilliO Group, Ltd.
[5]Kalcol 6870, manufactured by Kao Corporation
[6]Nikkol MGS-ASEV, manufactured by Nikko Chemicals Co., Ltd.
[7]Rheodol TW-O120V, manufactured by Kao Corporation
[8]Nikkol SMT, manufactured by Nikko Chemicals Co., Ltd.

From the results of Table 3, it is clear that the O/W emulsion emollient cream of Example 3 in accordance with the present invention is excellent in a usage sensation, as compared to the O/W emulsion emollient cream of Comparative Example 6.

Example 4 and Comparative Example 7

W/O Emulsion Emollient Cream

Polyglycerol fatty acid ester A is used as the composition for cosmetics of the present invention, Component A and Component B shown in Table 4 were mixed and heated to 80° C., thereby preparing an oily phase. Meanwhile, Component C was heated and dissolved at 80° C. to prepare an aqueous phase. The aqueous phase heated to the same temperature of 80° C. was added to the oily phase heated to 80° C. under stirring with a dispersion mixer, followed by cooling to room temperature to prepare a W/O emulsion emollient cream.

The resulting W/O emulsion emollient cream was evaluated according to the following evaluation method and evaluation criteria.

[Evaluation of Usage Sensation]

10 subjects were allowed to use the thus-prepared W/O emulsion emollient creams, and sensory evaluation for moist feeling and stickiness was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the cream with a grade of C or higher was rated as having passed the test.

Evaluation Criteria for Moist Feeling and Stickiness
A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 4

| Component | | Example 4 | Comparative Example 7 |
|---|---|---|---|
| | | | (unit: wt %) |
| A | Polyglycerol fatty acid ester A | 12.0 | — |
| | Triethyl hexanoin[1] | — | 12.0 |
| B | Dipentaerythrityl tripolyhydroxystearate[2] | 3.0 | 3.0 |
| | Hydrogenated polydecene[3] | 10.0 | 10.0 |
| | Cetyl dimethicone copolyol[4] | 1.5 | 1.5 |
| C | 1,3-BG | 10.0 | 10.0 |
| | Glycerol | 10.0 | 10.0 |
| | Sodium chloride | 1.0 | 1.0 |
| | Methylparaben | 0.1 | 0.1 |
| | Water | 52.4 | 52.4 |
| Evaluation | Moist feeling | A | B |
| | Stickiness | B | D |

[1]T.I.O, manufactured by The Nisshin OilliO Group, Ltd.
[2]Salacos WO-6, manufactured by The Nisshin OilliO Group, Ltd.
[3]Nomcort HP-30, manufactured by The Nisshin OilliO Group, Ltd.
[4]Abil EM 90, manufactured by Evonik Industries AG From the results of Table 4, it is clear that the W/O emulsion emollient cream of Example 4 in accordance with the present invention is excellent in a usage sensation, as compared to the W/O emulsion emollient cream of Comparative Example 7.

Example 5 and Comparative Example 8

Massage Gel

Polyglycerol fatty acid ester A is used as the composition for cosmetics of the present invention, Component A and Component B shown in Table 5 were mixed and heated to 80° C., thereby preparing an oily phase. Meanwhile, Component C was heated and dissolved at 80° C. to prepare a polyhydric alcohol phase. The oily phase heated to the same temperature of 80° C. was added to the polyhydric alcohol phase heated to 80° C., under stirring with a dispersion mixer, followed by cooling to room temperature to prepare a massage gel.

[Evaluation of Usage Sensation]

10 subjects were allowed to use the thus-prepared massage gels, and sensory evaluation for spreadability, moist feeling and stickiness was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the gel with a grade of C or higher was rated as having passed the test.

Evaluation Criteria for Spreadability, Moist Feeling and Stickiness

A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 5

| Component | | Example 5 | Comparative Example 8 |
|---|---|---|---|
| | | | (unit: wt %) |
| A | Polyglycerol fatty acid ester A | 18.0 | — |
| | Squalane | — | 18.0 |
| B | Mineral oil | 38.0 | 38.0 |
| C | Hydrogenated lecithin[1] | 1.0 | 1.0 |
| | 3-methyl-1,3-butanediol[2] | 10.0 | 10.0 |
| | Glycerol | 30.0 | 30.0 |
| | Water | 3.0 | 3.0 |
| Evaluation | Spreadability | A | D |
| | Moist feeling | B | C |
| | Stickiness | B | B |

[1]Basis LS-60HR, manufactured by The Nisshin OilliO Group, Ltd.
[2]Isopropylene glycol S, manufactured by Kuraray Co., Ltd.

From the results of Table 5, it is clear that the massage gel of Example 5 in accordance with the present invention is excellent in a usage sensation, as compared to the massage gel of Comparative Example 8.

Example 6 and Comparative Example 9

Cleansing Paste

Polyglycerol fatty acid ester A is used as the composition for cosmetics of the present invention, Component A and Component B shown in Table 6 were mixed and heated to 80° C., thereby preparing an oily phase. Meanwhile, Component C was heated and dissolved at 80° C. to prepare a polyhydric alcohol phase. The oily phase heated to the same temperature of 80° C. was added to the polyhydric alcohol phase heated to 80° C., under stirring with a dispersion mixer, followed by cooling to room temperature to prepare a cleansing paste.

[Evaluation of Cleansing Power]

Lip rouge was applied to an area of 2 cm×2 cm on the forearm, followed by being left for 30 minutes. The rouge-applied portion was massaged with 0.5 g of the cleansing paste for 30 seconds to detach makeup dirt and washed with flowing water. A detachment state of makeup dirt was visually evaluated according to the following evaluation criteria. The detachment state with a grade of C or higher was rated as having passed the test.

Evaluation Criteria of Cleansing Power

A: Completely detached
B: Almost detached
C: Slightly detached
D: Little detached

[Evaluation of Usage Sensation]

10 subjects were allowed to use the thus-prepared cleansing pastes, and sensory evaluation for compatibility with makeup dirt and a texture after washing with water was carried out based on a 3-point scale rating (good: 2, moderate: 1, and poor: 0). In addition, sensory evaluation values of individual subjects were totaled and subjected to a synthetic judgment.

The evaluation was carried out according to the following evaluation criteria and the paste with a grade of C or higher was rated as having passed the test.

Evaluation Criteria of Post-Wash Texture

A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 6

(unit: wt %)

| Component | | Example 6 | Comparative Example 9 |
|---|---|---|---|
| A | Polyglycerol fatty acid ester A | 14.0 | — |
|  | Squalane | — | 14.0 |
| B | Ethylhexyl palmitate[1] | 32.0 | 32.0 |
|  | Hydrogenated lecithin[2] | 1.0 | 1.0 |
|  | Glyceryl (behenate/eicosanedioate)[3] | 3.0 | 3.0 |
| C | Polyglyceryl-10 (behenate/eicosanedioate)[4] | 7.0 | 7.0 |
|  | Polyglyceryl-10 oleate[5] | 1.0 | 1.0 |
|  | Glycerol | 24.0 | 24.0 |
|  | 1,3-BG | 10.0 | 10.0 |
|  | Water | 8.0 | 8.0 |
| Evaluation | Cleansing power | B | B |
|  | Compatibility with makeup dirt | B | C |
|  | Post-wash texture | A | D |

[1] Salacos P-8, manufactured by The Nisshin OilliO Group, Ltd.
[2] Basis LS-60HR, manufactured by The Nisshin OilliO Group, Ltd.
[3] Nomcort HK-G, manufactured by The Nisshin OilliO Group, Ltd.
[4] Nomcort HK-P, manufactured by The Nisshin OilliO Group, Ltd.
[5] Salacos PG-180, manufactured by The Nisshin OilliO Group, Ltd.

From the results of Table 6, it is clear that the massage gel of Example 6 in accordance with the present invention has a cleansing power equivalent to the cleansing paste of Comparative Example 9 and is also excellent in a usage sensation.

Example 7 and Comparative Examples 10 to 11

Two-Separate-Layer-Type Make-Up Remover

Polyglycerol fatty acid ester A is used as the composition for cosmetics of the present invention, Component A and Component B shown in Table 7 were mixed, and Component C heated in advance to 70° C. was added thereto, thereby preparing a two-separate-layer-type make-up remover.

The resulting two-separate-layer-type make-up remover was evaluated according to the following evaluation method and evaluation criteria.

[Evaluation of Retention Time of Emulsified State]

In order to evaluate the retention time of an emulsified state of a two-separate-layer-type make-up remover, the two-separate-layer-type make-up remover was vigorously shaken 30 times to be uniformly mixed in a glass container, and left standing at room temperature, followed by measuring the retention time of an emulsified state. The retention time of an emulsified state was evaluated according to the following evaluation criteria and the remover with a grade of C or higher was rated as having passed the test.

The two-separate-layer-type make-up remover is used after gentle shaking to make transient emulsification of an oily phase and an aqueous phase. If the time taken for returning to the original state with separation of two layers is too short, this may lead to a problem in terms of usability. Therefore, it can be said that a longer retention time of an emulsified state of the two-separate-layer-type make-up remover is advantageous in terms of usability.

Evaluation Criteria of Retention Time of an Emulsified State

A: Retention time is 10 minutes or more.
B: Retention time is 5 minutes or more and less than 10 minutes.
C: Retention time is 3 minutes or more and less than 5 minutes.
D: Retention time is less than 3 minutes.

[Evaluation of Post-Wash Texture]

10 subjects were allowed to use the two-separate-layer-type make-up removers, and sensory evaluation of the texture after water washing of the two-separate-layer-type make-up removers was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the remover with a grade of C or higher was rated as having passed the test.

Evaluation Criteria for Synthetic Judgment of Post-Wash Texture

A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

[Evaluation of Post-Use External Appearance]

In order to evaluate the retention time of an emulsified state of a two-separate-layer-type make-up remover, the two-separate-layer-type make-up remover was vigorously shaken 30 times to be uniformly mixed in a glass container, and left standing at room temperature for 24 hours, followed by examination of external appearance. The external appearance was evaluated according to the following evaluation criteria and the remover with a grade of C or higher was rated as having passed the test.

Evaluation Criteria of External Appearance

A: Separation of both an upper layer and a lower layer in a colorless and transparent state
B: Slight turbidity observed in either of an upper layer and a lower layer
C: Some turbidity observed in either of an upper layer and a lower layer
D: Layer of emulsified materials observed
E: No separation, with retention of an emulsified state.

TABLE 7

(unit: wt %)

| Component | | Example 7 | Comparative Example 10 | Comparative Example 11 |
|---|---|---|---|---|
| A | Polyglycerol fatty acid ester A | 15.0 | — | — |
|  | Mineral oil | — | 15.0 | — |
|  | Diisostearyl malate[1] | — | — | 15.0 |
| B | Cyclomethicone[2] | 25.0 | 25.0 | 25.0 |
| C | 1,3-BG | 20.0 | 20.0 | 20.0 |
|  | Sodium chloride | 1.0 | 1.0 | 1.0 |
|  | Water | 39.0 | 39.0 | 39.0 |
| Evaluation | Retention time of emulsified state | B | D | B |
|  | Post-wash texture | A | C | E |
|  | Post-use external appearance | A | B | D |

[1] Cosmol 222, manufactured by The Nisshin OilliO Group, Ltd.
[2] SH-245, manufactured by Dow Corning Toray Co., Ltd.

From the results of Table 7, it is clear that the two-separate-layer-type make-up remover of Example 7 in accordance with the present invention is excellent in retention time of an emulsified state, a usage sensation and a post-use external appearance, as compared to the two-separate-layer-type make-up removers of Comparative Examples 10 and 11.

Example 8 and Comparative Example 12

Hair Conditioner

Polyglycerol fatty acid ester A is used as the composition for cosmetics of the present invention, Component A and Component B shown in Table 8 were mixed and heated to 70° C., and Component C heated in advance to 70° C. was added thereto, thereby preparing a hair conditioner.

The resulting hair conditioner was evaluated according to the following evaluation method and evaluation criteria.

[Evaluation of Hair Combability]

Hair was dipped in a 10% sodium lauryl sulfate aqueous solution and subjected to a damage treatment by ultrasonic irradiation. The hair was dipped in a 10% aqueous solution of the hair conditioner for 1 hour, and a resistance value when hair passed through a comb was measured using a rheometer (RT-2002 D·D, manufactured by Rheotec Co., Ltd.). The evaluation was carried out according to the following evaluation criteria and the resistance value with a grade of C or higher was rated as having passed the test.

Evaluation Criteria of Combability
A: maximum value of resistance is less than 0.3 kg.
B: Maximum value of resistance is 0.3 kg or more and less than 0.5 kg.
C: Maximum value of resistance is 0.5 kg or more and less than 1.0 kg.
D: Maximum value of resistance is 1.0 kg or more.

[Evaluation of Hair Manageability]

Hair was dipped in a 10% sodium lauryl sulfate aqueous solution and subjected to a damage treatment by ultrasonic irradiation. The hair was dipped in a 10% aqueous solution of the hair conditioner for 1 hour, washed with water, and then dried. 10 panelists were allowed to visually evaluate manageability of hair. The evaluation was carried out based on a 3-point scale rating (good: 2, moderate: 1, and poor: 0). In addition, evaluation values of individual panelists were totaled and subjected to a synthetic judgment. The evaluation was carried out according to the following evaluation criteria and the hair manageability with a grade of C or higher was rated as having passed the test.

Evaluation Criteria of Manageability
A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 8

(unit: wt %)

| Component | | Example 8 | Comparative Example 12 |
|---|---|---|---|
| A | Polyglycerol fatty acid ester A | 3.0 | — |
|   | Glyceryl tri(caprylate/caproate)[1] | — | 3.0 |
| B | Dipentaerythrityl hexa(hydroxystearate/stearate/rosinate)[2] | 3.0 | 3.0 |
|   | Stearyl alcohol[3] | 2.3 | 2.3 |
|   | Cetanol[4] | 1.5 | 1.5 |
|   | Dimethicone | 1.5 | 1.5 |
| C | Glycerol | 3.0 | 3.0 |
|   | Steartrimoniumammonium chloride (30% aqueous solution)[5] | 2.5 | 2.5 |
|   | Methylparaben | 0.1 | 0.1 |
|   | Water | 83.1 | 83.1 |
| Evaluation | Combability of hair | A | D |
|   | Manageability of hair | B | D |

[1] O.D.O, manufactured by The Nisshin OilliO Group, Ltd.
[2] Cosmol 168ARV, manufactured by The Nisshin OilliO Group, Ltd.
[3] Kalcol 688, manufactured by Kao Corporation
[4] Kalcol 6870, manufactured by Kao Corporation
[5] Quartamin 86W, manufactured by Kao Corporation From the results of Table 8, it is clear that the hair conditioner of Example 8 in accordance with the present invention is excellent in combability and manageability of hair, as compared to the hair conditioner of Comparative Example 12.

Example 9 and Comparative Examples 13 to 14

Lip Rouge

Polyglycerol fatty acid ester A is used as the composition for cosmetics of the present invention, and Component A and Component B shown in Table 9 were mixed, and heated and dissolved at 80° C. The mixture was poured into a mold, followed by cooling to prepare lip rouge.

The resulting lip rouge was evaluated according to the following evaluation method and evaluation criteria.

[Evaluation of Bitter Taste]

Bitter taste when lip rouge is put into the mouth was evaluated according to the following evaluation criteria and the lip rouge with a grade of C or higher was rated as having passed the test.

Evaluation Criteria of Bitter Taste
A: No feeling of bitter taste
B: Little feeling of bitter taste
C: Slight feeling of bitter taste
D: Feeling of bitter taste

[Evaluation of Spreadability, Stickiness and Lip Dryness]

10 subjects were allowed to use lip rouge, and sensory evaluation for spreadability, stickiness and lip dryness when used was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the lip rouge with a grade of C or higher was rated as having passed the test.

Evaluation Criteria for a Synthetic Judgment of Spreadability, Stickiness and Lip Dryness
A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 9

(unit: wt %)

| Component | | Example 9 | Comparative Example 13 | Comparative Example 14 |
|---|---|---|---|---|
| A | Polyglycerol fatty acid ester A | 32.0 | — | — |
|   | Diglyceryl sesquicaprylate[1] (hydroxyl value: 405) | — | 32.0 | — |

TABLE 9-continued

| Component | | Example 9 | Comparative Example 13 | Comparative Example 14 (unit: wt %) |
|---|---|---|---|---|
| | Tetraglyceryl pentastearate[2] (hydroxyl value: 35) | — | — | 32.0 |
| B | Diisostearyl malate[3] | 15.0 | 15.0 | 15.0 |
| | Dipentaerythrityl hexa (hydroxystearate/ stearate/ rosinate)[4] | 13.0 | 13.0 | 13.0 |
| | Hydrogenated polydecene[5] | 11.0 | 11.0 | 11.0 |
| | Candelilla wax | 8.0 | 8.0 | 8.0 |
| | Paraffin | 6.0 | 6.0 | 6.0 |
| | Beeswax | 3.0 | 3.0 | 3.0 |
| | Carnauba wax | 2.0 | 2.0 | 2.0 |
| | Pigment dispersion | 10.0 | 10.0 | 10.0 |
| Evaluation | Bitter taste | A | D | C |
| | Spreadability | A | B | E |
| | Stickiness | B | D | C |
| | Lip dryness | A | C | E |

[1] Salacos DG-158, manufactured by The Nisshin OilliO Group, Ltd.
[2] SY Glyster PS-3S, manufactured by Sakamoto Yakuhin Kogyo Co., Ltd.
[3] Cosmol 222, manufactured by The Nisshin OilliO Group, Ltd.
[4] Cosmol 168ARV, manufactured by The Nisshin OilliO Group, Ltd.
[5] Nomcort HP-30, manufactured by The Nisshin OilliO Group, Ltd.

[Evaluation of Bitter Taste]

Bitter taste when lip gloss is put into the mouth was evaluated according to the following evaluation criteria and the lip gloss with a grade of C or higher was rated as having passed the test.

Evaluation Criteria of Bitter Taste

A: No feeling of bitter taste
B: Little feeling of bitter taste
C: Slight feeling of bitter taste
D: Feeling of bitter taste

[Evaluation of Spreadability, Stickiness and Lip Dryness]

10 subjects were allowed to use lip gloss, and sensory evaluation for spreadability, stickiness and lip dryness when used was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the lip gloss with a grade of C or higher was rated as having passed the test.

Evaluation Criteria for a Synthetic Judgment of Spreadability, Stickiness and Lip Dryness A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 10

| Component | | Example 10 | Comparative Example 15 | Comparative Example 16 | Comparative Example 17 (unit: wt %) |
|---|---|---|---|---|---|
| A | Polyglycerol fatty acid ester A | 28.0 | — | — | — |
| | Diglyceryl sesquicaprylate[1] (hydroxyl value: 405) | — | 28.0 | — | — |
| | Hexaglyceryl pentastearate[2] (hydroxyl value: 93) | — | — | 28.0 | — |
| | Tetraglyceryl pentastearate (hydroxyl value: 35)[3] | — | — | — | 28.0 |
| B | Diisostearyl malate[4] | 20.0 | 20.0 | 20.0 | 20.0 |
| | Hydrogenated polyisobutene[5] | 50.0 | 50.0 | 50.0 | 50.0 |
| | Glyceryl (behenate/eicosanedioate)[6] | 2.0 | 2.0 | 2.0 | 2.0 |
| Evaluation | Bitter taste | A | D | C | C |
| | Spreadability | A | B | E | E |
| | Stickiness | B | B | E | E |
| | Lip dryness | A | D | E | E |

[1] Salacos DG-158, manufactured by The Nisshin OilliO Group, Ltd.
[2] SY Glyster PS-5S, manufactured by Sakamoto Yakuhin Kogyo Co., Ltd.
[3] SY Glyster PS-3S, manufactured by Sakamoto Yakuhin Kogyo Co., Ltd.
[4] Cosmol 222, manufactured by The Nisshin OilliO Group, Ltd.
[5] Parleam 18, manufactured by NOF Corporation
[6] Nomcort HK-G, manufactured by The Nisshin OilliO Group, Ltd.

From the results of Table 9, it is clear that the rouge of Example 9 in accordance with the present invention has no bitter taste and is excellent in a usage sensation, as compared to the rouge of Comparative Examples 13 and 14.

Example 10 and Comparative Examples 15 to 17

Lip Gloss

Polyglycerol fatty acid ester A is used as the composition for cosmetics of the present invention, and Component A and Component B shown in Table 10 were heated and dissolved at 80° C. to prepare lip gloss.

The resulting lip gloss was evaluated according to the following evaluation method and evaluation criteria.

From the results of Table 10, it is clear that the lip gloss of Example 10 in accordance with the present invention has no bitter taste and is excellent in a usage sensation, as compared to the lip gloss of Comparative Examples 15 to 17.

Example 11 and Comparative Example 18

W/O Emulsion Foundation

Polyglycerol fatty acid ester A is used as the composition for cosmetics of the present invention, and Component A, Component B and Component C shown in Table 11 were mixed and heated to 80° C., thereby preparing an oily phase. Meanwhile, Component D was heated and dissolved at 80° C. to prepare an aqueous phase. To the oily phase heated to 80° C., the aqueous phase heated to the same temperature of 80°

C. was added under stirring with a dispersion mixer, followed by cooling to room temperature to prepare a W/O emulsion foundation.

[Evaluation of Spreadability and Stickiness]

10 subjects were allowed to use W/O emulsion foundations, and sensory evaluation for spreadability and stickiness when used was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the foundation with a grade of C or higher was rated as having passed the test.

Evaluation Criteria for a Synthetic Judgment of Spreadability and Stickiness

A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 11

| Component | | Example 11 | Comparative Example 18 (unit: wt %) |
|---|---|---|---|
| A | Polyglycerol fatty acid ester A | 8.00 | — |
|   | Squalane | — | 8.00 |
| B | Dipentaerythrityl tripolyhydroxystearate[1] | 3.00 | 3.00 |
|   | Ethylhexyl p-methoxycinnamate[2] | 2.00 | 2.00 |
|   | Isostearic acid | 1.00 | 1.00 |
|   | Dimethicone | 6.00 | 6.00 |
|   | Cyclomethicone | 6.00 | 6.00 |
|   | Cetyl dimethicone copolyol[3] | 1.00 | 1.00 |
|   | PEG-10 dimethicone[4] | 1.00 | 1.00 |
|   | Propyl paraben | 0.10 | 0.10 |
| C | Talc | 2.70 | 2.70 |
|   | Titanium oxide | 8.40 | 8.40 |
|   | Iron oxide (yellow) | 0.60 | 0.60 |
|   | Iron oxide (red) | 0.18 | 0.18 |
|   | Iron oxide (black) | 0.12 | 0.12 |
| D | 1,3-BG | 10.00 | 10.00 |
|   | Glycerol | 2.00 | 2.00 |
|   | Methylparaben | 0.1 | 0.1 |
|   | Sodium chloride | 1.00 | 1.00 |
|   | Sodium hyaluronate (1% aqueous solution) | 1.00 | 1.00 |
|   | Water | 46.80 | 46.80 |
| Evaluation | Spreadability | A | D |
|   | Stickiness | B | D |

[1]Salacos WO-6, manufactured by The Nisshin OilliO Group, Ltd.
[2]Nomcort TAB, manufactured by The Nisshin OilliO Group, Ltd.
[3]Abil EM 90, manufactured by Evonik Industries AG
[4]KF6017, manufactured by Shin-Etsu Chemical Company From the results of Table 11, it is clear that the W/O emulsion foundations of Example 11 in accordance with the present invention is excellent in a usage sensation, as compared to the W/O emulsion foundation of Comparative Example 18.

Examples 12 to 13 and Comparative Example 19

Moisturizer

Individual components shown in Table 12 were mixed and heat-dissolved at 80° C., followed by cooling to room temperature, thereby preparing a moisturizer containing the composition for cosmetics of the present invention.

The resulting moisturizer was evaluated according to the following evaluation method and evaluation criteria.

[Evaluation of Water Retention Capacity]

20 g of each moisturizer was heated to 80° C. and mixed with 10 g of purified water at the same temperature of 80° C. The mixture was sufficiently stirred, cooled to room temperature, and placed in a Petri dish. The Petri dish was left in a constant temperature and humidity bath at a temperature of 25° C. and a relative humidity of 10% for 18 hours, and a decrease in moisture of the moisturizer was measured. The evaluation was carried out according to the following evaluation criteria and the moisturizer with a grade of C or higher was rated as having passed the test.

Evaluation Criteria of Water Retention Capacity

A: Post-storage weight is 90% or more of pre-storage weight.
B: Post-storage weight is 80% or more and less than 90% of pre-storage weight.
C: Post-storage weight is 70% or more and less than 80% of pre-storage weight.
D: Post-storage weight is less than 70% of pre-storage weight.

TABLE 12

| Component | | Example 12 | Example 13 | Comparative Example 19 (unit: wt %) |
|---|---|---|---|---|
| A | Polyglycerol fatty acid ester A | 1 | 4 | — |
| B | Dipropylene glycol | 10 | 15 | 10 |
| C | Polyoxyethylene hydrogenated castor oil (60E.O)[1] | 0.5 | 0.75 | 0.5 |
| D | Hydrogenated lecithin | — | 0.3 | — |
| Evaluation | Water retention capacity | B | A | D |

[1]Emanon CH-60, manufactured by Kao Corporation

From the results of Table 12, it is clear that the moisturizers of Examples 12 to 13 in accordance with the present invention are excellent in a water retention capacity, as compared to the moisturizer of Comparative Example 19.

Examples 14 to 18

Emulsion

Components A, B and C shown in Table 13 were heated and dissolved at 80° C., and the mixture was cooled to room temperature, thereby preparing compositions for cosmetics of the present invention. Meanwhile, Component D was heated and dissolved at 80° C. to prepare an aqueous phase. The aqueous phase heated to the same temperature of 60° C. was added to each of the compositions for cosmetics heated to 60° C., to prepare an emulsion.

The resulting emulsion was evaluated according to the following evaluation method and evaluation criteria.

[Measurement of Average Particle Diameter of Emulsion Particles]

The average particle diameter of the prepared emulsion was measured with a particle size distribution analyzer (LA-300, manufactured by Horiba Ltd.).

[Evaluation of Emulsion Stability]

Each of the thus-prepared emulsions was stored in a thermostatic bath at 40° C. for one month, followed by examination of changes in external appearance thereof. The emulsion stability was evaluated according to the following evaluation criteria. The emulsion with a grade of C or higher was rated as having passed the test.

Evaluation Criteria of Emulsion Stability
A: No separation
B: Little separation
C: Slight separation
D: Separation
E: Complete separation positions for cosmetics heated to 60° C., the aqueous phase heated to the same temperature of 60° C. was added to prepare an emulsion.

The resulting emulsion was evaluated according to the following evaluation method and evaluation criteria.

TABLE 13

(unit: wt %)

| Component | | Example 14 | Example 15 | Example 16 | Example 17 | Example 18 |
|---|---|---|---|---|---|---|
| A | Polyglycerol fatty acid ester A | 1 | 1 | 1 | 1 | 1 |
| B | Dipropylene glycol | 10 | 10 | 10 | 10 | — |
| C | Polyoxyethylene hydrogenated castor oil (25E.O)[1] | 0.5 | — | — | — | — |
| | Polyoxyethylene hydrogenated castor oil (40E.O)[2] | — | 0.5 | — | — | — |
| | Polyoxyethylene hydrogenated castor oil (60E.O)[3] | — | — | 0.5 | — | 0.5 |
| | Polyoxyethylene hydrogenated castor oil (80E.O)[4] | — | — | — | 0.5 | — |
| D | Methylparaben | 0.1 | 0.1 | 0.1 | 0.1 | 0.1 |
| | Water | 88.4 | 88.4 | 88.4 | 88.4 | 88.4 |
| | Dipropylene glycol | — | — | — | — | 10 |
| Evaluation | Average particle diameter of emulsion particles (μm) | 2.69 | 0.4 | 0.25 | 0.27 | 124.15 |
| | Emulsion stability | B | A | A | A | C |

[1] Emanon CH-25, manufactured by Kao Corporation
[2] Emanon CH-40, manufactured by Kao Corporation
[3] Emanon CH-60, manufactured by Kao Corporation
[4] Emanon CH-80, manufactured by Kao Corporation From the results of Table 13, it is clear that the emulsions of Examples 14 to 18 in accordance with the present invention exhibit an excellent emulsion stability.

Examples 19 to 23

Emulsion

Components A, B and C shown in Table 14 were mixed, heated and dissolved at 80° C., and the mixture was cooled to room temperature, thereby preparing compositions for cosmetics. Meanwhile, Component D was heated and dissolved at 80° C. to prepare an aqueous phase. To each of the com-

[Measurement of Average Particle Diameter of Emulsion Particles]

The average particle diameter of the prepared emulsion was measured with a particle size distribution analyzer (LA-300, manufactured by Horiba Ltd.).

[Evaluation of Emulsion Stability]

Each of the thus-prepared emulsions was stored in a thermostatic bath at 40° C. for one month, followed by examination of changes in external appearance thereof. The emulsion stability was evaluated according to the following evaluation criteria. The emulsion with a grade of C or higher was rated as having passed the test.

Evaluation Criteria of Emulsion Stability
A: No separation
B: Little separation
C: Slight separation
D: Separation
E: Complete separation

TABLE 14

(unit: wt %)

| Component | | Example 19 | Example 20 | Example 21 | Example 22 | Example 23 |
|---|---|---|---|---|---|---|
| A | Polyglycerol fatty acid ester A | 1 | 1 | 1 | 1 | 1 |
| B | Dipropylene glycol | — | — | — | 10 | 10 |
| | Octanediol[1] | 10 | — | — | — | — |
| | Hexanediol[2] | — | 10 | — | — | — |
| | 2-ethylhexanol | — | — | 10 | — | — |
| C | Polyoxyethylene hydrogenated castor oil (60E.O) | 0.5 | 0.5 | 0.5 | — | — |
| | Sodium lauryl sulfate | — | — | — | 0.5 | — |
| | Distearyldimonium chloride | — | — | — | — | 0.5 |
| D | Methylparaben | 0.1 | 0.1 | 0.1 | 0.1 | 0.1 |
| | Water | 88.4 | 88.4 | 88.4 | 88.4 | 88.4 |

TABLE 14-continued (unit: wt %)

| Component | | Example 19 | Example 20 | Example 21 | Example 22 | Example 23 |
|---|---|---|---|---|---|---|
| Evaluation | Average particle diameter of emulsion particles (μm) | 0.55 | 0.24 | 56.71 | 86.68 | 7.67 |
| | Emulsion stability | A | A | C | C | C |

[1] Adeka Nol Og, manufactured by ADEKA
[2] KMO-6, manufactured by Kankohsha

From the results of Table 14, it is clear that the emulsions of Examples 19 to 23 in accordance with the present invention exhibit an excellent emulsion stability.

Examples 24 to 25

Emulsion

Components A, B and C shown in Table 15 were mixed, heated and dissolved at 80° C., and the mixture was cooled to room temperature, thereby preparing compositions for cosmetics. Meanwhile, Component D was heated and dissolved at 80° C. to prepare an aqueous phase. Each of the compositions for cosmetics heated to the same temperature of 60° C. was added to the aqueous phase heated to 60° C., to prepare an emulsion.

The resulting emulsion was evaluated according to the following evaluation method and evaluation criteria.

[Evaluation of Emulsion Stability]

Each of the thus-prepared emulsions was stored in a thermostatic bath at 40° C. for one month, followed by examination of changes in external appearance thereof. The emulsion stability was evaluated according to the following evaluation criteria. The emulsion with a grade of C or higher was rated as having passed the test.

Evaluation Criteria of Emulsion Stability
A: No separation
B: Little separation
C: Slight separation
D: Separation
E: Complete separation

TABLE 15

(unit: wt %)

| Component | | Example 24 | Example 25 |
|---|---|---|---|
| A | Polyglycerol fatty acid ester A | 1 | 1 |
| B | Dipropylene glycol | 10 | — |
| C | Polyoxyethylene hydrogenated castor oil (60E.O) | 0.5 | 0.5 |
| D | Methylparaben | 0.1 | 0.1 |
| | Water | 88.4 | 88.4 |
| | Dipropylene glycol | — | 10 |
| Evaluation | Average particle diameter of emulsion particles (μm) | 0.15 | 19.61 |
| | Emulsion stability | A | C |

From the results of Table 15, it is clear that the emulsions of Examples 24 to 25 in accordance with the present invention exhibit an excellent emulsion stability.

Examples 26 to 28

Emulsion

Component A shown in Table 16 was heated and dissolved at 80° C., followed by cooling to room temperature, thereby preparing compositions for cosmetics. Meanwhile, Component B was heated and dissolved at 80° C. to prepare an aqueous phase. The aqueous phase heated to the same temperature of 60° C. was added to each of the compositions for cosmetics heated to 60° C., followed by cooling to 40° C. Thereafter, Component C and Component D were added thereto, followed by stirring and then cooling to room temperature, thereby preparing an emulsion.

The resulting emulsion was evaluated according to the following evaluation method and evaluation criteria.

[Measurement of Viscosity of Emulsion]

The viscosity of the thus-prepared emulsion was measured using a BL type viscometer at 25° C.

[Evaluation of Emulsion Stability]

Each of the thus-prepared emulsions was stored in a thermostatic bath at 40° C. for one month, followed by examination of changes in external appearance thereof. The emulsion stability was evaluated according to the following evaluation criteria. The emulsion with a grade of C or higher was rated as having passed the test.

Evaluation Criteria of Emulsion Stability
A: No separation
B: Little separation
C: Slight separation
D: Separation
E: Complete separation

[Evaluation of Texture]

10 subjects were allowed to use emulsions, and sensory evaluation of texture was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the emulsion with a grade of C or higher was rated as having passed the test.

Evaluation Criteria for a Synthetic Judgment of Moisturizing Feeling and Freshness
A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 16

(unit: wt %)

| Component | | Example 26 | Example 27 | Example 28 |
|---|---|---|---|---|
| A | Polyglycerol fatty acid ester A | 3.0 | 3.0 | 3.0 |
| | Dipropylene glycol | 15.0 | 15.0 | 15.0 |
| | Polyoxyethylene hydrogenated castor oil (80E. O) | 1.0 | 1.0 | 1.0 |
| | Hydrogenated lecithin | 0.3 | 0.3 | 0.3 |
| B | Glycerol | 4.0 | 4.0 | 2.0 |
| | 1,3-propanediol | 6.0 | 5.0 | 5.0 |

TABLE 16-continued

| Component | | Example 26 | Example 27 | (unit: wt %) Example 28 |
|---|---|---|---|---|
| | Methylparaben | 0.1 | 0.1 | 0.1 |
| | Water | 58.0 | 54.0 | 56.0 |
| C | 1% sodium hydroxide aqueous solution | 2.6 | 2.6 | 2.6 |
| D | 1% carbomer aqueous solution | 10.0 | 10.0 | 10.0 |
| | 1% xanthan gum aqueous solution | — | 5.0 | 5.0 |
| | Viscosity (mPa · s) | 550 | 1410 | 1480 |
| Evaluation | Emulsion stability | A | A | A |
| | Moisturizing feeling | A | A | A |
| | Gloss | A | B | B |

From the results of Table 16, it is clear that the emulsions of Examples 26 to 28 in accordance with the present invention are excellent in emulsion stability and moisturizing feeling.

Example 29 and Comparative Example 20

Bath Cosmetic (Emulsion Type)

Components A, B, C, D and E shown in Table 17 were mixed, heated and dissolved at 80° C., and the mixture was cooled to room temperature, thereby preparing compositions for cosmetics. Meanwhile, Component F was heated and dissolved at 80° C. to prepare an aqueous phase. To each of the compositions for cosmetics heated to 60° C., the aqueous phase heated to the same temperature of 60° C. was added, followed by cooling to room temperature, thereby preparing a bath cosmetic (emulsion type).

The resulting bath cosmetic was evaluated according to the following evaluation method and evaluation criteria.
[Evaluation of Emulsion Stability]
Each of the thus-prepared bath cosmetics (emulsion type) was stored in a thermostatic bath at 40° C. for one month, followed by examination of changes in external appearance thereof. The emulsion stability was evaluated according to the following evaluation criteria. The bath cosmetic with a grade of C or higher was rated as having passed the test.
Evaluation Criteria of Emulsion Stability
A: No separation
B: Little separation
C: Slight separation
D: Separation
E: Complete separation
[Evaluation of in-Bath Dispersibility]
Each of the thus-prepared bath cosmetics (emulsion type) (20 ml) was introduced to a bath (200 L) at 40° C. and manually stirred for 3 seconds, followed by examination of the state thereof. The evaluation was carried out according to the following evaluation criteria and the bath cosmetic with a grade of C or higher was rated as having passed the test.
Evaluation Criteria of in-Bath Dispersibility
A: Rapid and uniform dispersion
B: Uniform dispersion within 10 seconds after being stirred
C: Uniform dispersion within 30 seconds after being stirred
D: Oily phase substances being suspended
[Evaluation of Usage Sensation]
Each of the-thus prepared bath cosmetics (emulsion type) (20 ml) was dispersed in a bath (200 L) at 40° C. 10 subjects were allowed to take a bath for 10 minutes, and sensory evaluation for post-bathing moist feeling and stickiness was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the bath cosmetic with a grade of C or higher was rated as having passed the test.
Evaluation Criteria of Moist Feeling and Stickiness
A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

TABLE 17

| Component | | Example 29 | (unit: wt %) Comparative Example 20 |
|---|---|---|---|
| A | Polyglycerol fatty acid ester A | 27.5 | — |
| | Squalane | — | 27.5 |
| B | Glycerol | 15.0 | 15.0 |
| | 1,3-propanediol | 5.0 | 5.0 |
| C | Polyglyceryl-10 myristate | 0.5 | 0.5 |
| D | Hydrogenated lecithin | 0.5 | 0.5 |
| E | Water | 1.5 | 1.5 |
| F | Methylparaben | 0.1 | 0.1 |
| | Water | 49.9 | 49.9 |
| Evaluation | Emulsion stability | A | D |
| | In-bath dispersibility | B | A |
| | Moist feeling | A | A |
| | Stickiness | A | B |

From the results of Table 17, it is clear that the bath cosmetic (emulsion type) of Example 29 in accordance with the present invention exhibits an excellent emulsion stability and an equivalent texture, as compared to the bath cosmetic (emulsion type) of Comparative Example 20.

Example 30 and Comparative Examples 21 to 22

Emulsion

Component A shown in Table 18 was mixed and heated to 70° C., thereby preparing a polyhydric alcohol phase. Meanwhile, Component B including polyglycerol fatty acid ester A as the composition for cosmetics of the present invention was heated to 70° C. to prepare an oily phase. The oily phase heated to the same temperature of 70° C. was added to the polyhydric alcohol phase heated to 70° C. under stirring with a dispersion mixer. Then, the mixture was cooled to 40° C. and Component C was further added thereto, followed by cooling to room temperature, thereby preparing an emulsion.

The resulting emulsion was evaluated according to the following evaluation method and evaluation criteria.
[Measurement of Average Particle Diameter of Emulsion Particles]
The average particle diameter of the prepared emulsion was measured with a particle size distribution analyzer (LA-300, manufactured by Horiba Ltd.).
[Evaluation Method and Evaluation Criteria for Emulsion Stability of Emulsion]
Each of the thus-prepared emulsions was centrifuged using a centrifuge (Model No.: 6800, manufactured by Kubota Corp.) at 5000 rpm for 15 minutes, followed by examination of the external appearance thereof. The emulsion stability was evaluated according to the following evaluation criteria. The emulsion with a grade of C or higher was rated as having passed the test.

Evaluation Criteria of Emulsion Stability
A: No separation
B: Little separation
C: Slight separation
D: Separation
E: Complete separation

[Evaluation of Usage Sensation]

10 subjects were allowed to use the thus-prepared emulsions, and sensory evaluation for moist feeling and stickiness was carried out based on a 3-point scale rating (good: 2, moderate: 1, and poor: 0). In addition, sensory evaluation values of individual subjects were totaled and subjected to a synthetic judgment. The evaluation was carried out according to the following evaluation criteria and the emulsion with a grade of C or higher was rated as having passed the test.

Evaluation Criteria for Moist Feeling and Stickiness
A: Total score is 18 points or more.
B: Total score is 15 points or more and less than 18 points.
C: Total score is 12 points or more and less than 15 points.
D: Total score is 10 points or more and less than 12 points.
E: Total score is less than 10 points.

[Measurement of Viscosity of Emulsion]

The viscosity of the thus-prepared emulsion was measured using a BL type viscometer at 25° C.

TABLE 18

| Component | | Example 30 | Comparative Example 21 | Comparative Example 22 |
|---|---|---|---|---|
| | | (unit: wt %) | | |
| A | Sucrose fatty acid ester[1] | 0.15 | 0.15 | 0.15 |
| | Glycerol | 0.75 | 0.75 | 0.75 |
| | 1,3-propanediol | 0.25 | 0.25 | 0.25 |
| | Water | 0.10 | 0.10 | 0.10 |
| B | Polyglycerol fatty acid ester A | 3.75 | — | — |
| | Squalane | — | 3.75 | — |
| | Glyceryl tri(caprylate/caproate) | — | — | 3.75 |
| C | 1,3-propanediol | 4.75 | 4.75 | 4.75 |
| | Water | 80.25 | 80.25 | 80.25 |
| | Ethanol | 10.00 | 10.00 | 10.00 |
| Evaluation | Average particle* diameter of emulsion particles (μm) | 0.52 | 0.50 | 0.61 |
| | Emulsion stability | A | E | E |
| | Moist feeling | A | B | C |
| | Stickiness | A | D | C |
| | Viscosity (mPa·s) | 2 | 2 | 2 |

[1]DK Ester F-160, manufactured by Dai-ichi Kogyo Seiyaku Co., Ltd.

From the results of Table 18, it is clear that the emulsion of Example 30 in accordance with the present invention is excellent in emulsion stability and a usage sensation, as compared to the emulsions of Comparative Examples 21 and 22.

INDUSTRIAL APPLICABILITY

The composition for cosmetics of the present invention can be preferably used in the field of cosmetic production.

The invention claimed is:

1. A composition for cosmetics comprising:
   a polyglycerol caprylate, which is an ester of polyglycerol having an average degree of polymerization of 4 to 100 with a caprylic acid, has a hydroxyl value equal to or less than 15 mgKOH/g, and has a specific gravity at 20° C. of 0.96 to 1.15; and
   a polyhydric alcohol.

2. The composition for cosmetics according to claim 1, wherein the polyglycerol constituting the polyglycerol caprylate has an average degree of polymerization of 4 to 10.

3. The composition for cosmetics according to claim 2, wherein the polyglycerol constituting the polyglycerol caprylate has an average degree of polymerization of 6.

4. The composition for cosmetics according to claim 1, wherein the polyglycerol caprylate has a hydroxyl value of 10 mgKOH/g or less.

5. The composition for cosmetics according to claim 1, further comprising a non-ionic surfactant.

6. The composition for cosmetics according to claim 5, wherein the non-ionic surfactant is a polyoxyethylene hydrogenated castor oil.

7. The composition for cosmetics according to claim 5, further comprising a hydrogenated lecithin.

8. The composition for cosmetics according to claim 1, wherein the polyhydric alcohol is at least one selected from the group consisting of dipropylene glycol, octanediol, 1,3-propanediol and hexanediol.

9. The composition for cosmetics according to claim 1, wherein the composition for cosmetics is for a skin care cosmetic, a bath cosmetic, or a hair cosmetic.

10. A cosmetic comprising the composition for cosmetics according to claim 1.

11. The cosmetic according to claim 10, wherein the cosmetic is a two-separate-layer-type cosmetic, or an emulsion cosmetic.

12. A method of producing an oil-in-water emulsion cosmetic, comprising mixing the composition for cosmetics according to claim 1 with a hydrophilic solution and emulsifying the mixture.

13. A two-separate-layer-type cosmetic comprising the composition for cosmetics according to claim 1 and water, packaged in a transparent or translucent container.

* * * * *